United States Patent
Spohn et al.

(10) Patent No.: US 11,865,294 B2
(45) Date of Patent: Jan. 9, 2024

(54) FLUID CONTROL VALVE AND MANIFOLD

(71) Applicant: BAYER HEALTHCARE LLC, Whippany, NJ (US)

(72) Inventors: Michael Spohn, Fenelton, PA (US); Kevin Cowan, Allison Park, PA (US); Brian Cain, Elizabeth, PA (US); David Berry, Kittanning, PA (US); James Fentress, Creedmoor, NC (US); David Orenstein, Apex, NC (US); James Dedig, Pittsburgh, PA (US); Barry Tucker, Verona, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 611 days.

(21) Appl. No.: 16/342,161

(22) PCT Filed: Oct. 16, 2017

(86) PCT No.: PCT/US2017/056757
§ 371 (c)(1),
(2) Date: Apr. 15, 2019

(87) PCT Pub. No.: WO2018/075390
PCT Pub. Date: Apr. 26, 2018

(65) Prior Publication Data
US 2019/0232041 A1 Aug. 1, 2019

Related U.S. Application Data

(60) Provisional application No. 62/513,413, filed on May 31, 2017, provisional application No. 62/463,200, (Continued)

(51) Int. Cl.
*A61M 39/22* (2006.01)
*A61M 5/20* (2006.01)
(Continued)

(52) U.S. Cl.
CPC .......... *A61M 39/223* (2013.01); *A61M 5/007* (2013.01); *A61M 5/2066* (2013.01);
(Continued)

(58) Field of Classification Search
CPC .......... A61M 39/223; A61M 2039/224; A61M 5/31; A61M 5/19; A61M 5/1407;
(Continued)

(56) References Cited

U.S. PATENT DOCUMENTS 4,096,879 A  6/1978 Serur et al.
4,331,140 A  5/1982 Hallsey et al.
(Continued)

FOREIGN PATENT DOCUMENTS

CN   102003424 A   4/2011
CN   102548606 A   7/2012
(Continued)

OTHER PUBLICATIONS

English Translation of Quendt et al. (WO 2009/003500) (Year: 2009).*
(Continued)

*Primary Examiner* — Nilay J Shah
(74) *Attorney, Agent, or Firm* — David Schramm; Joseph L. Kent; James R. Stevenson

(57) ABSTRACT

A fluid control valve for use in a fluid delivery system for delivering fluid to a patient includes a valve body defining an internal chamber, a first inlet port for receiving a first inlet tube, a second inlet port for receiving a second inlet tube, an outlet port, and a sliding valve member slidably disposed in the internal chamber. The first inlet tube defines a first inlet lumen axially aligned with the internal chamber. The second inlet tube defines a second inlet lumen axially aligned with the internal chamber. The sliding valve member includes a first sealing end and second sealing end. The sliding valve
(Continued)

member is positionable in a first operating state, a second operating state, and a third operating state based on a flow differential between the first inlet lumen and the second inlet lumen.

16 Claims, 29 Drawing Sheets

Related U.S. Application Data filed on Feb. 24, 2017, provisional application No. 62/409,054, filed on Oct. 17, 2016.

(51) Int. Cl.
| | |
|---|---|
| *A61M 5/00* | (2006.01) |
| *A61M 5/31* | (2006.01) |
| *A61M 5/14* | (2006.01) |
| *A61M 5/168* | (2006.01) |
| *A61M 39/24* | (2006.01) |

(52) U.S. Cl.
CPC .............. *A61M 5/31* (2013.01); *A61M 5/1408* (2013.01); *A61M 5/16827* (2013.01); *A61M 2039/224* (2013.01); *A61M 2039/242* (2013.01); *A61M 2039/2433* (2013.01)

(58) Field of Classification Search
CPC ................. A61M 5/1408; A61M 39/24; A61M 2039/2433; A61M 2039/242; A61M 5/16827; A61M 5/2066; A61M 5/31596; A61M 3/005; F16K 3/265; F16K 3/00; F16K 11/00; F16K 11/02; F16K 11/022; F16K 11/06; F16K 11/065; F16K 11/0716
See application file for complete search history.

(56) References Cited

U.S. PATENT DOCUMENTS

| | | | |
|---|---|---|---|
| 4,631,055 A * | 12/1986 | Redl | A61B 17/00491 |
| | | | 222/135 |
| 4,759,527 A * | 7/1988 | Brown | A61M 5/14526 |
| | | | 251/324 |
| 4,828,551 A | 5/1989 | Gertler et al. | |
| 5,490,499 A | 2/1996 | Heinonen et al. | |
| 5,739,508 A | 4/1998 | Uber, III | |
| 6,365,080 B1 * | 4/2002 | Parise | B29C 48/13 |
| | | | 264/167 |
| 6,595,950 B1 | 7/2003 | Miles et al. | |
| 7,306,736 B2 | 12/2007 | Collins et al. | |
| 7,308,300 B2 | 12/2007 | Toews et al. | |
| 7,462,166 B2 | 12/2008 | Kowan et al. | |
| 7,475,701 B2 | 1/2009 | Trocki et al. | |
| 8,096,316 B2 | 1/2012 | Trocki et al. | |
| 8,261,777 B2 | 9/2012 | Doig | |
| 8,551,037 B2 | 10/2013 | Suchecki et al. | |
| 9,265,885 B2 | 2/2016 | Strobl | |
| 9,498,570 B2 | 11/2016 | Cowan et al. | |
| 9,526,829 B2 | 12/2016 | Spohn et al. | |
| 9,555,379 B2 | 1/2017 | Schriver et al. | |
| 9,901,671 B2 | 2/2018 | Toews et al. | |
| 2004/0055652 A1 | 3/2004 | Erickson | |
| 2004/0060999 A1 | 4/2004 | Kock | |
| 2006/0009739 A1 | 1/2006 | Poutiatine et al. | |
| 2006/0047368 A1 | 3/2006 | Maharajh et al. | |
| 2007/0083152 A1 | 4/2007 | Williams, Jr. et al. | |
| 2007/0129705 A1 | 6/2007 | Trombley, III | |
| 2007/0219480 A1 | 9/2007 | Kamen et al. | |
| 2007/0219597 A1 | 9/2007 | Kamen et al. | |
| 2007/0272311 A1 | 11/2007 | Trocki et al. | |
| 2008/0041452 A1 | 2/2008 | Zweber | |
| 2008/0077081 A1 | 3/2008 | Mounce et al. | |
| 2008/0172006 A1 | 7/2008 | Hicks | |
| 2008/0195082 A1 * | 8/2008 | Pauser | B65D 81/325 |
| | | | 604/518 |
| 2008/0281278 A1 | 11/2008 | Williams, Jr. et al. | |
| 2009/0149743 A1 | 6/2009 | Barron et al. | |
| 2009/0177180 A1 | 7/2009 | Rubalcaba, Jr. et al. | |
| 2009/0187083 A1 * | 7/2009 | Blatcher | A61B 5/15003 |
| | | | 600/309 |
| 2010/0147403 A1 * | 6/2010 | Bresnahan | F15B 13/028 |
| | | | 137/528 |
| 2010/0217232 A1 | 8/2010 | Rosenblatt | |
| 2011/0021905 A1 | 1/2011 | Patrick et al. | |
| 2011/0061752 A1 * | 3/2011 | Hu | F16K 11/0716 |
| | | | 137/605 |
| 2011/0218495 A1 | 9/2011 | Remde | |
| 2012/0220949 A1 * | 8/2012 | Davies | A61M 5/3294 |
| | | | 604/191 |
| 2013/0049976 A1 | 2/2013 | Maggiore | |
| 2013/0075222 A1 | 3/2013 | Ari | |
| 2013/0123619 A1 | 5/2013 | Griggs | |
| 2014/0188050 A1 * | 7/2014 | Dittrich | A61M 5/19 |
| | | | 604/191 |
| 2014/0261809 A1 | 9/2014 | Rife | |
| 2015/0011975 A1 * | 1/2015 | Anderson | A61M 5/31596 |
| | | | 604/506 |
| 2015/0202361 A1 | 7/2015 | Burns et al. | |
| 2015/0202426 A1 | 7/2015 | Spohn et al. | |
| 2015/0335821 A1 | 11/2015 | Griffth et al. | |
| 2016/0243346 A1 * | 8/2016 | Vasko | A61M 39/286 |
| 2017/0100577 A1 | 4/2017 | Spohn et al. | |

FOREIGN PATENT DOCUMENTS

| | | | |
|---|---|---|---|
| EP | 0323321 A1 | 7/1989 | |
| JP | S63151149 U | 10/1988 | |
| JP | H11299889 A | 11/1999 | |
| WO | 8103689 A1 | 12/1981 | |
| WO | 9800186 A1 | 1/1998 | |
| WO | 0200291 A1 | 1/2002 | |
| WO | 2006089157 A2 | 8/2006 | |
| WO | 2006108775 A2 | 10/2006 | |
| WO | 2007002613 A2 | 1/2007 | |
| WO | 2007092618 A2 | 8/2007 | |
| WO | WO-2009003500 A1 * | 1/2009 | ............ F15B 13/028 |
| WO | 2012061140 A1 | 5/2012 | |
| WO | 2013126318 A1 | 8/2013 | |
| WO | 2015126526 A1 | 8/2015 | |
| WO | 2015134717 A2 | 9/2015 | |
| WO | 2015164783 A1 | 10/2015 | |
| WO | 2016069711 A1 | 5/2016 | |
| WO | 2016069714 A1 | 5/2016 | |
| WO | 2016172467 A1 | 10/2016 | |
| WO | 2018053074 A1 | 3/2018 | |

OTHER PUBLICATIONS

"International Preliminary Report on Patentability from PCT Application No. PCT/US2017/056757", dated May 2, 2019.
Harvard Apparatus, Harvard Peristaltic Pump, Dec. 2012, www.harvardapparatus.com, Holliston, MA.

* cited by examiner

FLUID CONTROL VALVE AND MANIFOLD

CROSS REFERENCE TO RELATED APPLICATIONS

The present application is a 371 national phase application of PCT International Application No. PCT/US2017/056757, filed Oct. 16, 2017, and claims priority to U.S. Provisional Patent Application No. 62/409,054, filed Oct. 17, 2016, entitled "Fluid Control Valve and Manifold", U.S. Provisional Patent Application No. 62/463,200, filed Feb. 24, 2017, entitled "Syringe Cap", and U.S. Provisional Patent Application No. 62/513,413, filed May 31, 2017, entitled "Sliding Mixing Valve For Dual Syringe Medical Injector", the disclosures of all of which are hereby incorporated herein by reference in their entirety.

BACKGROUND OF THE DISCLOSURE

Field of the Disclosure

The present disclosure relates generally to fluid control valves and manifolds for use in a multi-syringe fluid injector. More specifically, the disclosure relates to fluid control valves and manifolds for substantially isolating fluid pressure in a first syringe from fluid pressure in a second syringe based on a pressure differential between the first syringe and the second syringe. Additionally, the disclosure relates to a fluid control valve and manifold for mixing fluids from a first syringe and a second syringe during a multi-fluid injection protocol.

Description of the Related Art

In many medical diagnostic and therapeutic procedures, a medical practitioner, such as a physician, injects a patient with one or more medical fluids. In recent years, a number of injector-actuated syringes and powered fluid injectors for pressurized injection of medical fluids, such as an imaging contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other imaging procedures. In general, these fluid injectors are designed to deliver a preset amount of fluid at a preset pressure and/or flow rate.

Typically, fluid injectors have drive members, such as pistons, that connect to a syringe plunger within the syringe. The syringe generally includes a rigid barrel with the syringe plunger being slidably disposed within the barrel. The drive members drive the plungers in a proximal and/or distal direction relative to a longitudinal axis of the barrel to draw fluid into the syringe barrel or deliver the fluid from the syringe barrel.

Syringes for use with fluid injectors may be made of various medical-grade plastic materials. During certain injection procedures, the syringe barrel wall may change volume as a function of the fluid injection pressure due to excessive radial expansion under such pressure. Fluid injectors having at least one pressure jacket have been developed for enclosing the syringe while in use and preventing radial expansion of the syringe due to buildup of fluid pressure within the syringe.

In fluid injection systems having multiple syringes, the problem of inaccurate volume delivery may be further exacerbated when fluids from the multiple syringes are injected simultaneously at different pressures. For example, contrast media may be injected at a higher pressure than saline to achieve the same flow rate because the contrast media may have a higher viscosity than saline. As a result of the pressure differential between the two fluids, the fluid injected under higher pressure may tend to bleed into the lower pressure side of the system. As a result, some amount of delivery volume is lost due to the expansion, or capacitance, of the lower pressure side components. Conventional shuttle valves are known which isolate fluids under pressure during injection procedures. However, these valves do not generally provide for dual flow where mixtures of the two or more fluids are injected at the same time.

It would be desirable to provide an improved fluid injection system which could isolate the lower pressure side from the higher pressure side of the system in order to reduce or eliminate inaccurate volume delivery associated with the pressure differential between two fluids of the fluid injection system, while allowing for dual flow when injections of mixtures of the two or more fluids are desired.

SUMMARY OF THE DISCLOSURE

The present disclosure generally relates to a fluid control valve and manifold for substantially isolating fluid pressure in a first syringe from fluid pressure in a second syringe based on a pressure differential between the first syringe and the second syringe. Additionally, the present disclosure generally relates to a fluid control valve and manifold for mixing fluids from a first syringe and a second syringe during a multi-fluid injection protocol.

In some examples, the present disclosure is directed to a fluid control valve for use in a fluid delivery system for delivering fluid to a patient. The fluid control valve includes a valve body defining an internal chamber, a first inlet port for receiving a first inlet tube, a second inlet port for receiving a second inlet tube, an outlet port, and a sliding valve member slidably disposed in the internal chamber. The first inlet tube defines a first inlet lumen axially aligned with the internal chamber. The second inlet tube defines a second inlet lumen axially aligned with the internal chamber. The sliding valve member includes a first sealing end and a second sealing end. The sliding valve member is positionable in a first operating state, a second operating state, and a third operating state based on a flow differential between the first inlet lumen and the second inlet lumen. The sliding valve member and the valve body define at least one channel, the at least one channel providing fluid communication between the second inlet lumen and the outlet port in the first operating state, the at least one channel providing fluid communication between the first inlet lumen and the outlet port in the second operating state, and the at least one channel providing fluid communication between the first inlet lumen, the second inlet lumen, and the outlet port in the third operating state.

In some examples, in the first operating state, the first sealing end of the sliding valve member engages the first inlet tube and isolates the first inlet lumen from the second inlet lumen and the outlet port. In the second operating state, the second sealing end of the sliding valve member engages the second inlet tube and isolates the second inlet lumen from the first inlet lumen and the outlet port. In the third operating state, the sliding valve member allows fluid communication between the first inlet lumen, the second inlet lumen, and the outlet port.

In some examples, the sliding valve member includes at least one flange member extending radially from a body of the sliding valve member.

In some examples, the sliding valve member includes at least two flange members including a first flange member adjacent to the first sealing end and a second flange member adjacent to the second sealing end.

In some examples, at least a portion of the at least one flange member is deflectable when sufficient fluid flow is applied to a surface of the flange member. Deflection of the deflectable portion of the at least one flange member allows fluid communication between the first inlet lumen and the outlet port or between the second inlet lumen and the outlet port.

In some examples, the at least one flange member comprises one or more deflectable flange members. The deflectable flange members deflect to a lower flow side in response to a flow differential between the first inlet lumen and the second inlet lumen.

In some examples, deflection of any of the one or more deflectable flange members increases a drag coefficient of the sliding valve member.

In some examples, at least one flange member further includes one or more rigid flange members.

In some examples, at least a portion of the at least one flange member is rigid.

In some examples, the at least one channel includes at least one mixing feature configured to provide turbulent mixing at a confluence point of a first fluid from the first inlet lumen and a second fluid from the second inlet lumen.

In some examples, the mixing feature includes a helical groove.

In some examples, the mixing feature includes a first helical groove and a second helical groove having opposite directionality.

In some examples, the sliding valve member includes a first sliding valve member and a second sliding valve member independently slidable in the internal chamber of the valve body.

In other examples, the present disclosure is directed to a syringe connector manifold assembly. The syringe connector manifold assembly includes a fluid control valve, a first syringe end cap, a second syringe end cap, a first inlet tube providing fluid communication between a first inlet port of the fluid control valve and the second syringe end cap, and a second inlet tube providing fluid communication between a second inlet port of the fluid control valve and the second syringe end cap. The fluid control valve includes a sliding valve member positionable in a first operating state, a second operating state, and a third operating state based on a flow differential between the first inlet tube and the second inlet tube. The sliding valve member defines at least one channel, the at least one channel providing fluid communication between the second inlet port and an outlet port in the first operating state, the at least one channel providing fluid communication between the first inlet port and the outlet port in the second operating state, and the at least one channel providing fluid communication between the first inlet port, the second inlet port, and the outlet port in the third operating state.

In some examples, the syringe connector manifold further includes a first selectable valve providing fluid communication between the first inlet tube and a first bulk fluid source and a second selectable valve providing fluid communication between the second inlet tube and a second bulk fluid source.

In some examples, the fluid control valve includes at least one mixing feature configured to provide turbulent mixing at a confluence point of a first fluid injected through the first inlet tube and a second fluid injected through the second inlet tube.

In some examples, the syringe connector manifold assembly further includes a delivery tube set configured to provide fluid communication between the outlet port of the fluid control valve and a patient.

In accordance with other examples, the disclosure of the present application may be characterized by one or more of the following clauses:

Clause 1: A fluid control valve for use in a fluid delivery system for delivering fluid to a patient, the fluid control valve comprising: a valve body defining an internal chamber; a first inlet port for receiving a first inlet tube, wherein the first inlet tube defines a first inlet lumen axially aligned with the internal chamber; a second inlet port for receiving a second inlet tube, wherein the second inlet tube defines a second inlet lumen axially aligned with the internal chamber; an outlet port; and a sliding valve member slidably disposed in the internal chamber, the sliding valve member comprising a first sealing end and second sealing end; wherein the sliding valve member is positionable in a first operating state, a second operating state, and a third operating state based on a flow differential between the first inlet lumen and the second inlet lumen; and wherein the sliding valve member and the valve body define at least one channel, the at least one channel providing fluid communication between the second inlet lumen and the outlet port in the first operating state, the at least one channel providing fluid communication between the first inlet lumen and the outlet port in the second operating state, and the at least one channel providing fluid communication between the first inlet lumen, the second inlet lumen, and the outlet port in the third operating state.

Clause 2: The fluid control valve of clause 1, wherein, in the first operating state, the first sealing end of the sliding valve member engages the first inlet tube and isolates the first inlet lumen from the second inlet lumen and the outlet port; wherein, in the second operating state, the second sealing end of the sliding valve member engages the second inlet tube and isolates the second inlet lumen from the first inlet lumen and the outlet port; and wherein, in the third operating state, the sliding valve member allows fluid communication between the first inlet lumen, the second inlet lumen, and the outlet port.

Clause 3: The fluid control valve of any of clauses 1 or 2, wherein the sliding valve member comprises at least one flange member extending radially from a body of the sliding valve member.

Clause 4: The fluid control valve of clause 3, wherein the sliding valve member comprises at least two flange members comprising a first flange member adjacent to the first sealing end and a second flange member adjacent to the second sealing end.

Clause 5: The fluid control valve of clause 3, wherein at least a portion of the at least one flange member is deflectable when sufficient fluid flow is applied to a surface of the flange member, wherein deflection of the deflectable portion of the at least one flange member allows fluid communication between the first inlet lumen and the outlet port or between the second inlet lumen and the outlet port.

Clause 6: The fluid control valve of clause 3, wherein the at least one flange member comprises one or more deflectable flange members, wherein the deflectable flange members deflect to a lower flow side in response to a flow differential between the first inlet lumen and the second inlet lumen.

Clause 7: The fluid control valve of clauses 5 or 6, wherein deflection of any of the one or more deflectable flange members increases a drag coefficient of the sliding valve member.

Clause 8: The fluid control valve of clauses 6 or 7, wherein the at least one flange member further comprises one or more rigid flange members.

Clause 9: The fluid control valve of clauses 4 or 5, wherein at least a portion of the at least one flange member is rigid.

Clause 10: The fluid control valve of any of clauses 1 to 9, wherein the at least one channel comprises at least one mixing feature configured to provide turbulent mixing at a confluence point of a first fluid from the first inlet lumen and a second fluid from the second inlet lumen.

Clause 11: The fluid control valve of clause 10, wherein the at least one mixing feature comprises a helical groove.

Clause 12: The fluid control valve of clause 10, wherein the at least one mixing feature comprises a first helical groove and a second helical groove having opposite directionality.

Clause 13: The fluid control valve of any of clauses 1 to 12, wherein the sliding valve member comprises a first sliding valve member and a second sliding valve member independently slidable in the internal chamber of the valve body.

Clause 14: A syringe connector manifold assembly comprising: fluid control valve; a first syringe end cap; a second syringe end cap; a first inlet tube providing fluid communication between a first inlet port of the fluid control valve and the second syringe end cap; and a second inlet tube providing fluid communication between a second inlet port of the fluid control valve and the second syringe end cap; wherein the fluid control valve comprises a sliding valve member positionable in a first operating state, a second operating state, and a third operating state based on a flow differential between the first inlet tube and the second inlet tube; and wherein the sliding valve member defines at least one channel, the at least one channel providing fluid communication between the second inlet port and an outlet port in the first operating state, the at least one channel providing fluid communication between the first inlet port and the outlet port in the second operating state, and the at least one channel providing fluid communication between the first inlet port, the second inlet port, and the outlet port in the third operating state.

Clause 15: The syringe connector manifold assembly of clause 14, further comprising: a first selectable valve providing fluid communication between the first inlet tube and a first bulk fluid source; and a second selectable valve providing fluid communication between the second inlet tube and a second bulk fluid source.

Clause 16: The syringe connector manifold assembly of clause 14 or 15, wherein the fluid control valve comprises at least one mixing feature configured to provide turbulent mixing at a confluence point of a first fluid injected through the first inlet tube and a second fluid injected through the second inlet tube.

Clause 17: The syringe connector manifold assembly of any of clauses 14 to 16, further comprising a delivery tube set configured to provide fluid communication between the outlet port of the fluid control valve and a patient.

These and other features and characteristics of fluid control valves and manifolds for dual syringe medical injectors, as well as the methods of operation and functions of the related elements of structures and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only.

DETAILED DESCRIPTION

Figure 1:
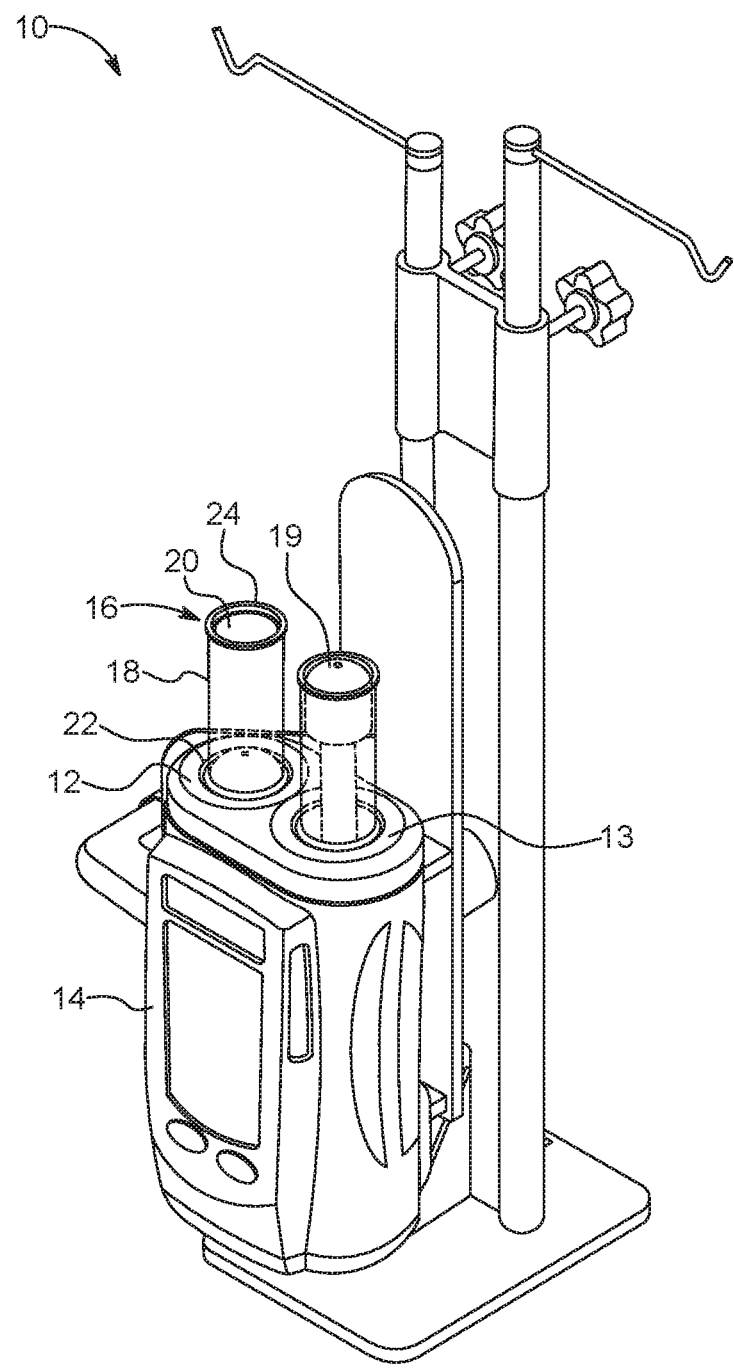
FIG. 1 is a front perspective view of a fluid injector having a pair of pressure jackets for use with the fluid control valve of the present disclosure.

As used in the specification, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the components as they are oriented in the drawing figures.

Spatial or directional terms, such as "left", "right", "inner", "outer", "above", "below", and the like, are not to be considered as limiting as the invention can assume various alternative orientations.

When used in relation to a syringe and/or a pressure jacket, the term "proximal" refers to a portion of a syringe and/or a pressure jacket nearest to an injector when a syringe and/or a pressure jacket is oriented for connecting to an injector. The term "distal" refers to a portion of a syringe and/or a pressure jacket farthest away from an injector when a syringe and/or a pressure jacket is oriented for connecting to an injector. The term "radial" refers to a direction in a cross-sectional plane normal to a longitudinal axis of a syringe and/or a pressure jacket extending between proximal and distal ends. The term "circumferential" refers to a direction around an inner or outer surface of a sidewall of a syringe and/or a pressure jacket.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The term "at least" means "greater than or equal to".

The term "substantially perpendicular" means "perpendicular plus or minus 5 degrees". The term "substantially parallel" means "parallel plus or minus 5 degrees".

The term "includes" is synonymous with "comprises".

It is to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

All documents, such as but not limited to issued patents and patent applications, referred to herein, and unless otherwise indicated, are to be considered to be "incorporated by reference" in their entirety.

Referring to the drawings in which like reference characters refer to like parts throughout the several views thereof, the present disclosure is generally directed to a fluid control valve and manifold for substantially isolating fluid pressure in a first syringe from fluid pressure in a second syringe based on a pressure differential between the first syringe and the second syringe.

With reference to FIG. 1, a fluid injector 10 includes at least one injector head 12 and an injector housing 14. The injector head 12 may be supported on a support structure 13. In some examples, such as shown in FIG. 1, the fluid injector 10 may include two injector heads 12 arranged in a side-by-side orientation. Each injector head 12 may be formed at a front end of the injector housing 14 and may be configured for receiving and retaining at least one syringe and/or pressure jacket 16. While FIG. 1 illustrates the fluid injector 10 with two injector heads 12, each with a corresponding syringe and/or pressure jacket 16, other examples of the fluid injector 10 may include one injector head or more than two injector heads with a corresponding number of syringes and/or pressure jackets.

With continued reference to FIG. 1, each injector head 12 includes a drive member 19, such as a reciprocally driven piston moved by a motor (not shown) which is operated by a controller (not shown). Each drive member 19 may be configured to extend into and from the respective injector head 12 through an opening in the front end of the injector housing 14. The drive members 19 impart a motive force to at least a portion of the syringes, optionally disposed in respective pressure jackets 16, as described herein. In some examples, the drive members 19 may impart motive force to plungers of corresponding syringes having rigid sidewalls.

Figure 2:
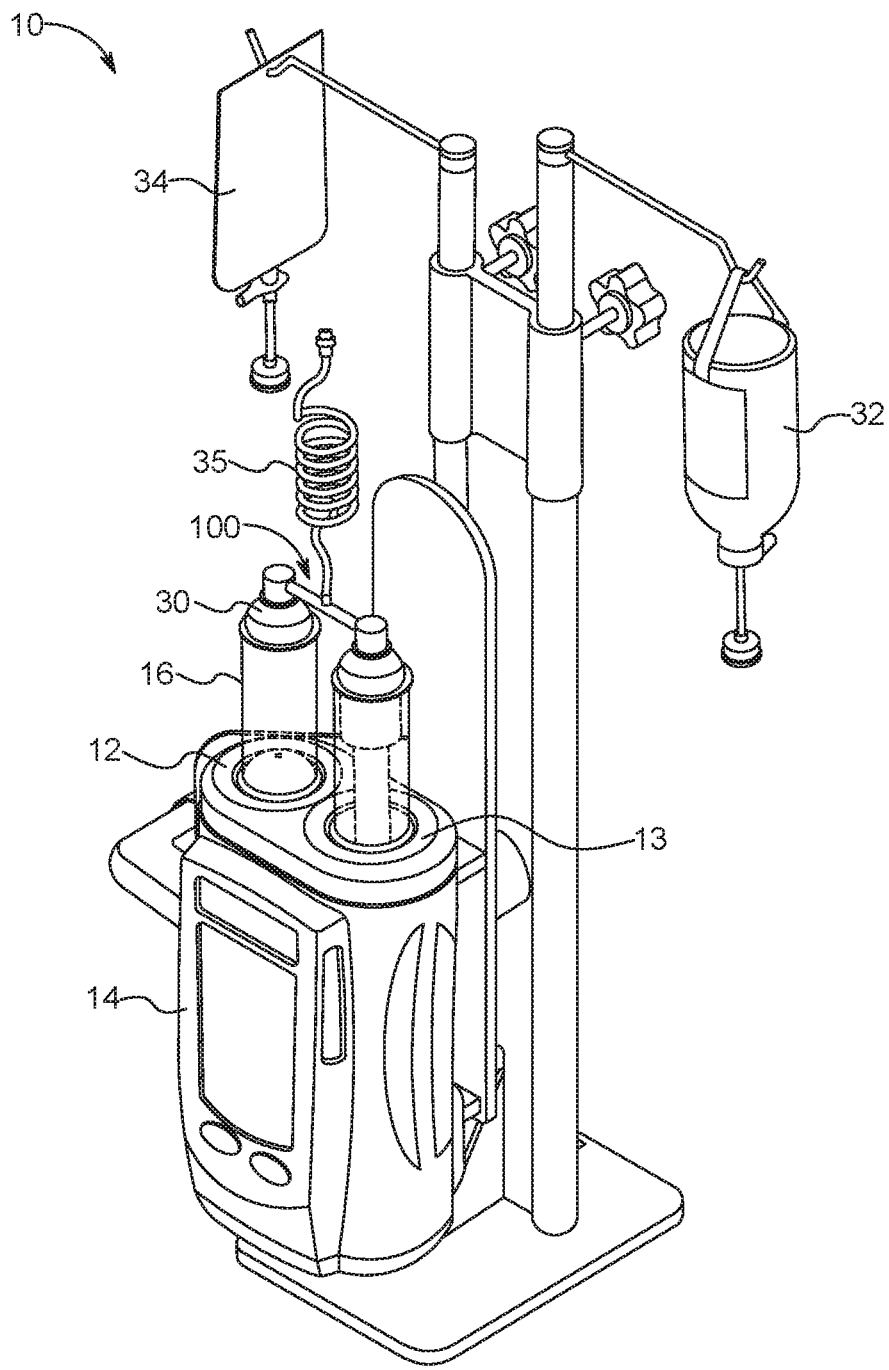
FIG. 2 is a perspective front view of the fluid injector of FIG. 1 shown with a syringe installed in each pressure jacket and a fluid control valve in accordance with one example of the present disclosure.

With reference to FIG. 2, the fluid injector 10 is configured to receive a syringe 30 within each pressure jacket 16. The at least one pressure jacket 16 is typically a reusable multiple-use component, while the syringe 30 is typically a single-use component. The fluid injector 10 may have at least one bulk fluid source for filling the syringes 30 with fluid. The bulk fluid source may be a first bulk fluid source 32 containing a first medical fluid, such as a contrast imaging agent, and a second bulk fluid source 34 containing a second medical fluid, such as saline, for separately filling the syringes 30 with first or second fluid contained in the first and second bulk fluid sources 32, 34, respectively. At least one fluid path set 35 may be fluidly connected with a discharge end of each syringe 30 for delivering fluid from the syringes 30 through tubing connected to a catheter, needle, or other fluid delivery connection (not shown) inserted into a patient at a vascular access site. Fluid flow into and from the at least one syringe 30 may be regulated by a fluid control module (not shown). The fluid control module may operate various pistons, valves, and/or flow regulating structures to regulate the delivery of the medical fluid, such as saline solution and/or contrast, to the patient based on user selected injection parameters, such as injected medical fluid, injection flow rate, duration, total injection volume, and/or ratio of contrast media and saline. Examples of suitable front-loading fluid injectors that may be used or modified for use with the herein-described system, including at least one pressure jacket 16 and syringe 30, are disclosed in International Patent Application Nos. PCT/US2015/027582; PCT/US2016/028824; and PCT/US2017/051473, the disclosures of which are incorporated herein by reference. Other suitable injectors include, for example, conventional single- and dual-head injectors for injecting contrast and/or saline, such as during a medical imaging procedure. Examples of suitable conventional injectors include, for example, the MEDRAD Salient Injector (Bayer HealthCare LLC); the MEDRAD Stellant Injector (Bayer HealthCare LLC, Indianola, PA); and the MRXperion Injector (Bayer HealthCare LLC, Indianola, PA).

With reference to FIG. 1, the at least one pressure jacket 16 is mounted to the front end of the injector housing 14 by an attachment mechanism (not shown) that allows for removable connection of the at least one pressure jacket 16 with the injector housing 14. Suitable pressure jacket/injector attachment mechanisms are described in International Patent Application Nos. PCT/US2015/057747 and PCT/US2015/057751, the disclosures of which are incorporated herein by reference. In some examples, the at least one pressure jacket 16 may be non-removably connected to the injector housing 14. The at least one pressure jacket 16 may have a generally hollow cylindrical shape with a front or distal end 18 having a syringe receiving opening 20 for receiving the syringe 30 (shown in FIG. 2) into the pressure jacket 16. The at least one pressure jacket 16 further includes a rear or proximal end 22 configured to engage at least a portion of the fluid injector 10 and removably or non-removably connect the at least one pressure jacket 16 to the fluid injector 10. The at least one pressure jacket 16 has a sidewall 24 extending between the distal end 18 and the proximal end 22 along a longitudinal axis of the at least one pressure jacket 16. The opening 20 at the distal end 18 of the at least one pressure jacket 16 defines a throughbore that extends between the distal end 18 and the proximal end 22.

The at least one pressure jacket 16 may be made from a material capable of restraining an outward radial expansion of the syringe 30 due to pressurization during an injection procedure. As discussed previously, the syringe 30 itself may not be capable of withstanding the high pressures associated with certain fluid injection procedures. The at least one pressure jacket 16 may be used to limit the radial expansion of the syringe 30. In some examples, the at least one pressure jacket 16 may be made from a medical grade material, such as medical grade plastic, metal, or glass. In certain examples, the at least one pressure jacket 16 may be manufactured from a translucent or transparent material so that at least a portion of a syringe 30 may be observed through the sidewall 24. An interior surface of the throughbore 26 is configured to contact at least a portion of an exterior surface of the syringe 30. The at least one pressure jacket 16 has an inner diameter sized to receive the outer diameter of the syringe 30 such that the syringe 30 can be easily inserted into and removed from the throughbore 26.

The syringe 30 is adapted for use in CT, MRI, PET, and like imaging procedures and operable at typical operating pressures of, for example, about 10-400 psi, such as 200-400 psi, depending on the viscosity of the fluid and the desired rate of injection. In some examples, the syringe 30 may be configured for use in procedures requiring pressures on the order of 1,200 psi, such as angiography. In some aspects, the syringe 30 may be a syringe disclosed in International Patent Application No. PCT/US2015/027582 and/or International Patent Application No. PCT/US2016/028824, the disclosures of which are incorporated herein by reference in their entireties.

Figure 3:
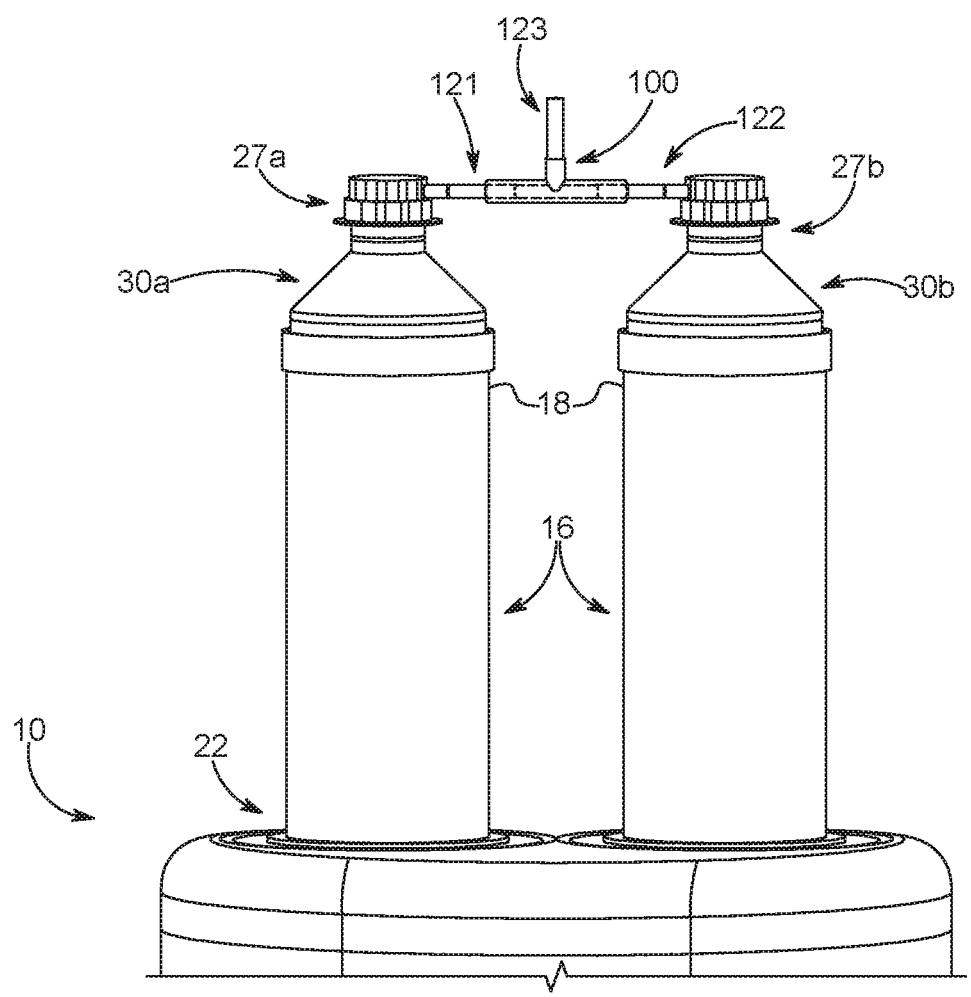
FIG. 3 is a detailed perspective view of the syringes, pressure jackets, and fluid control valve shown in FIG. 2.

With reference to FIG. 3, the fluid injector 10 having a fluid control valve 100 in accordance with various aspects of the present disclosure is shown. The fluid control valve 100 may be in fluid communication between a first syringe 30a and a second syringe 30b, each optionally contained in a pressure jacket 16. The fluid control valve 100 may connect to a first inlet tube 121 terminating in an end cap 27a of the first syringe 30a, and a second inlet tube 122 terminating in an end cap 27b of the second syringe 30b. Alternatively, the first inlet tube 121 and the second inlet tube 122 may be connected to the distal tip of the syringe, for example with a luer-type fitting or other conventional connection mechanism. The first syringe 30a and the second syringe 30b and their respective pressure jackets 16 are mounted to the fluid injector 10, as described above, for injecting one or more medical fluids into a patient. For example, the fluid injector 10 may inject saline from the first syringe 30a and a contrast agent from the second syringe 30b.

In examples for procedures requiring a dual-flow of a mixture of contrast and saline, it is desirable to mix the contrast and saline fluids prior to injecting the dual fluid mixture into the patient. Mixing allows a substantially uniform solution of contrast and saline to be delivered to the patient during the dual-flow portion of the injection procedure, with no major changes in contrast concentrations and/or saline concentrations over the time of the injection. In addition, dilution of the viscous contrast with the less viscous saline by mixing may also allow for less applied pressures to achieve desired flow rates. During portions of a fluid injection procedure requiring injection of either contrast or saline, i.e., single-flow, flow of one of the two or more injection fluids may be selected by stopping any applied pressure on the syringe containing the non-desired injection fluid. In such a case, it is also desirable to shut off fluid communication between the active syringe and the inactive syringe to prevent back-flow and mixing of the injected fluid with the non-injected fluid within the inactive syringe. According to various aspects of the present disclosure, fluid control valve 100 includes a valve mechanism that allows for single-flow of one of the medical fluids without back-flow into the inactive syringe, for example by shutting off fluid communication with the inactive syringe, and also allows for dual-flow of both fluids during a dual-flow portion of an injection procedure, optionally with turbulent mixing of the two medical fluids.

Figure 4:
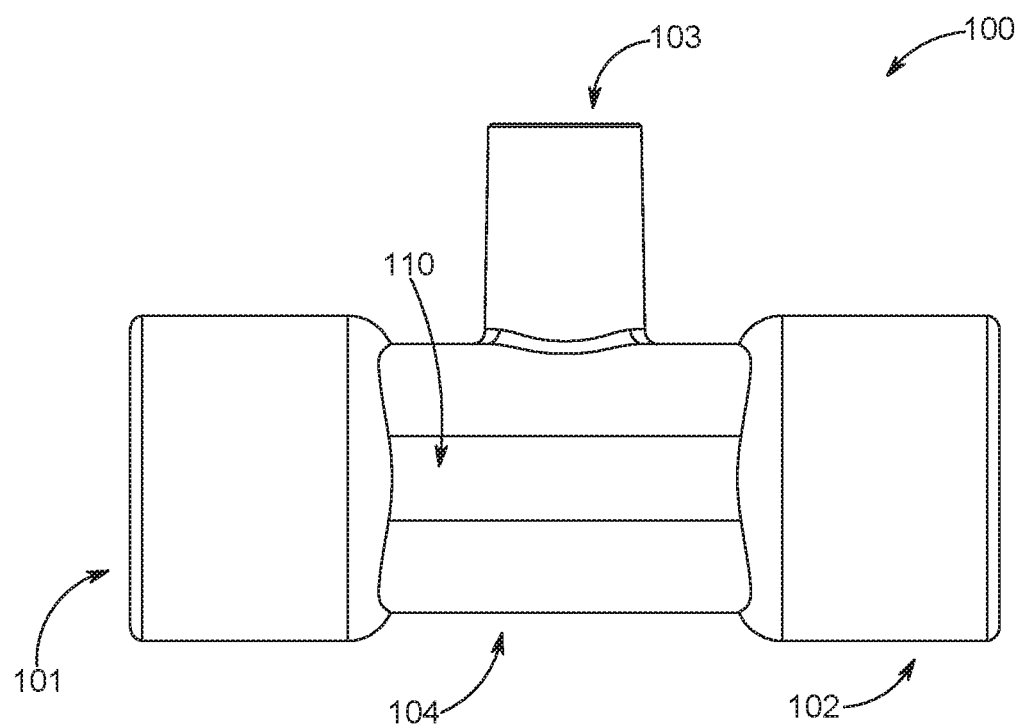
FIG. 4 is a front view of the fluid control valve in accordance with one example of the present disclosure.
Figure 5:
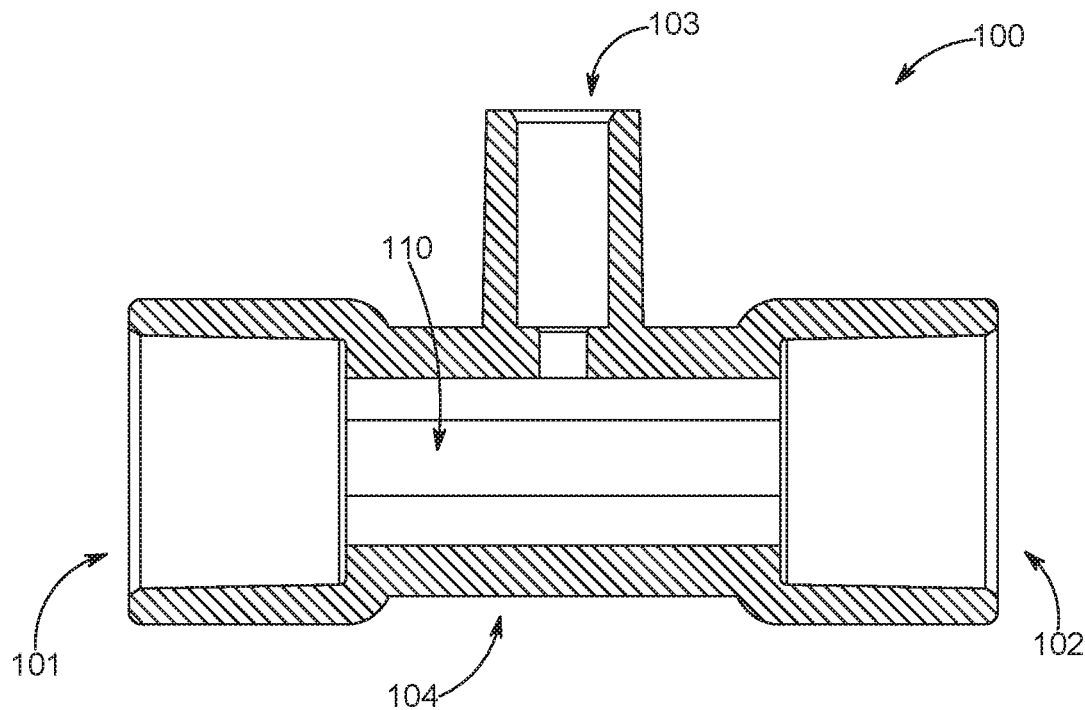
FIG. 5 is a front sectional view of the fluid control valve of FIG. 4 with the sliding valve member removed for clarity.

With reference to FIGS. 4-5, according to certain aspects, the fluid control valve 100 includes a valve body 104 which defines an internal chamber 110. A first inlet port 101 for fluid communication between a first syringe and the internal chamber 110, a second inlet port 102 for fluid communication between a second syringe and the internal chamber 110, and an outlet port 103 are in fluid communication with the internal chamber 110. In certain aspects, the internal chamber 110 may generally be in axial alignment with the first inlet port 101 and the second inlet port 102. The internal chamber 110 has a constant cross-sectional area such that a sliding valve member 200 (see FIGS. 6A-9) may freely slide axially within the internal chamber 110 in response to a pressure differential from the fluid in the first syringe and the second syringe.

Figure 6A:
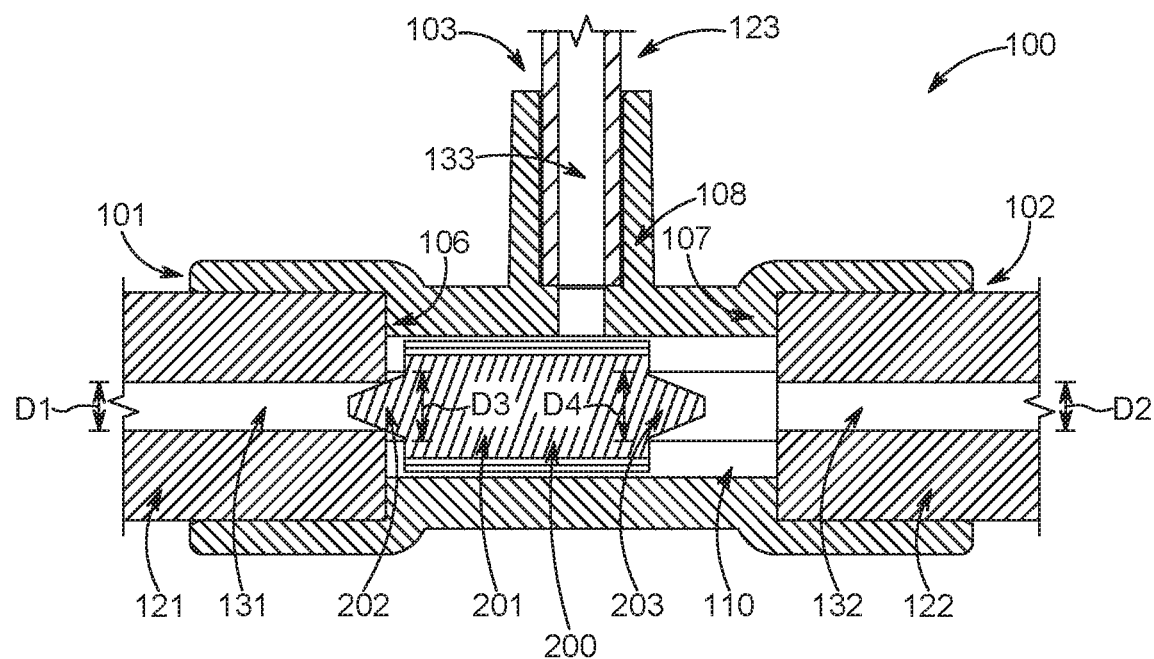
FIG. 6A is a front sectional view of the fluid control valve of FIG. 4 with a sliding valve member in accordance with one example of the present disclosure, shown in a first operating state.
Figure 6B:
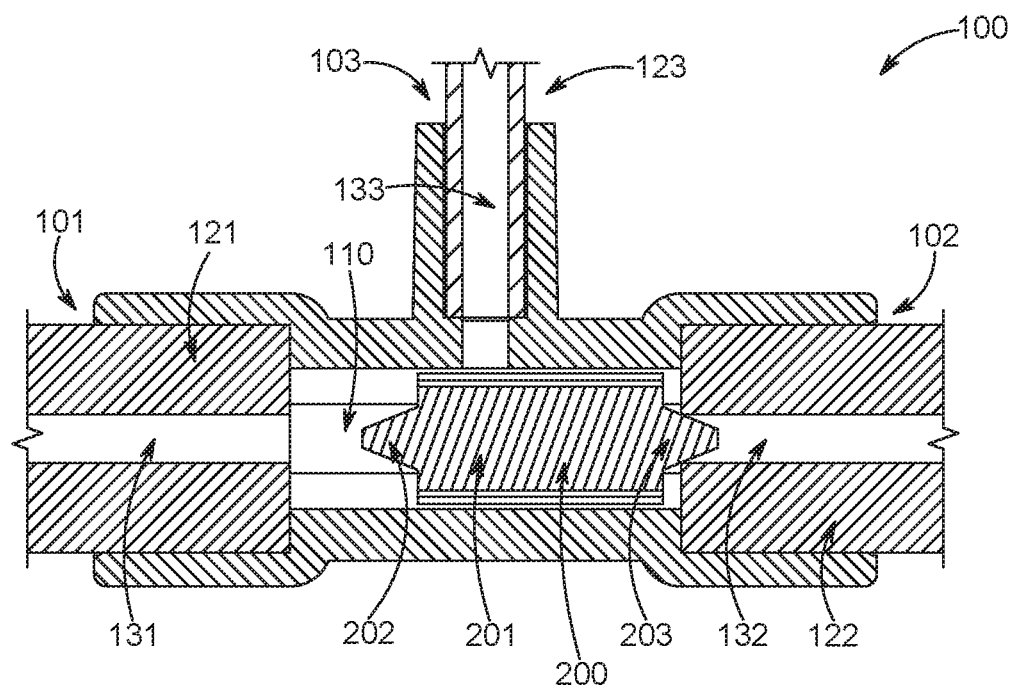
FIG. 6B is a front sectional view of the fluid control valve of FIG. 6A, shown in a second operating state.
Figure 6C:
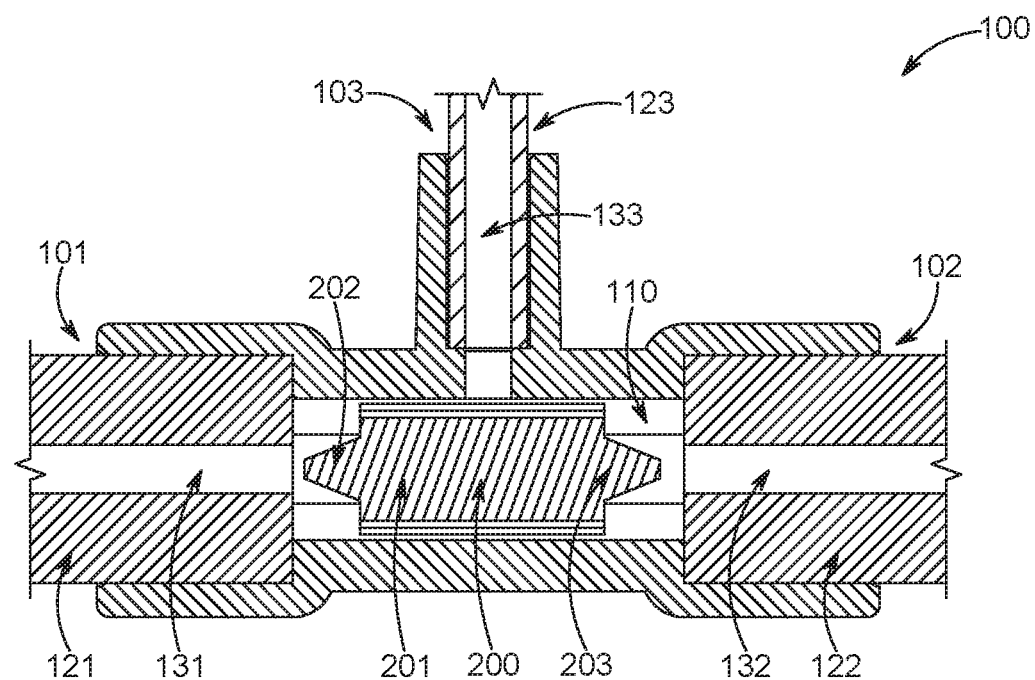
FIG. 6C is a front sectional view of the fluid control valve of FIG. 6A, shown in a third operating state.
Figure 7:
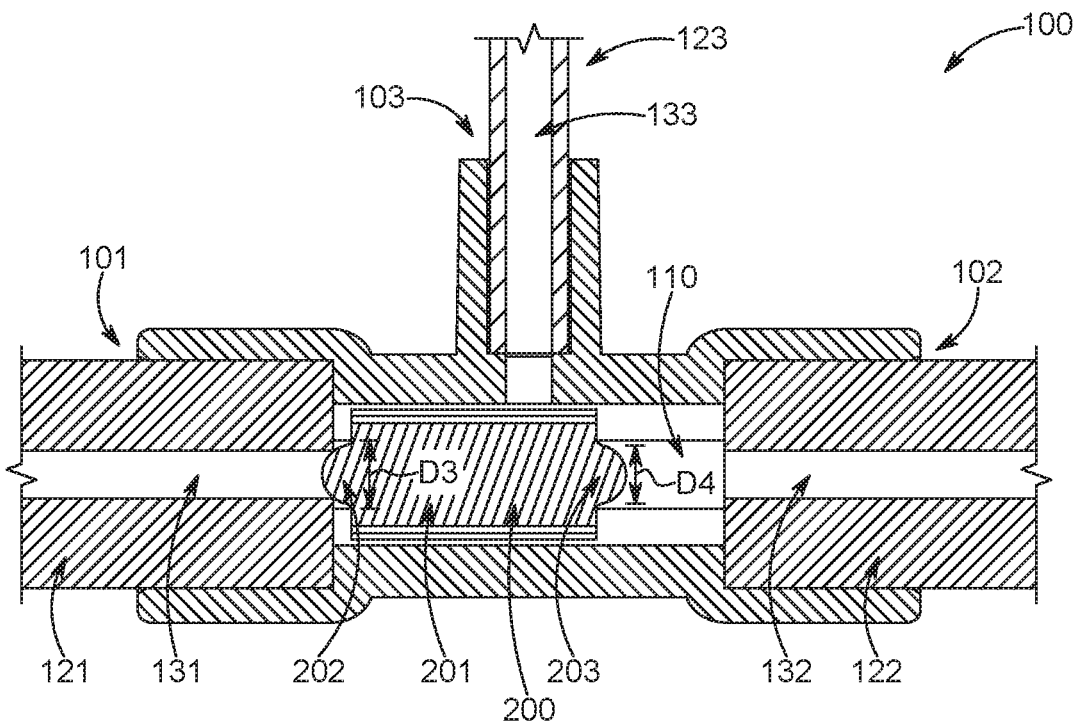
FIG. 7 is a front sectional view of the fluid control valve of FIG. 4 with a sliding valve member in accordance with another example of the present disclosure.

With reference to FIGS. 6A-7, the first inlet port 101 is adapted for receiving a first inlet tube 121, the second inlet port 102 is adapted for receiving a second inlet tube 122, and the outlet port 103 is adapted to receive an outlet tube 123. The first inlet tube 121, the second inlet tube 122, and the outlet tube 123 define a first inlet lumen 131, a second inlet lumen 132, and an outlet lumen 133, respectively. The first inlet tube 121 engages a first shoulder 106 of the first inlet port 101, the second inlet tube 122 engages a second shoulder 107 of the second inlet port 102, and the outlet tube 123 engages a third shoulder 108 of the outlet port 103. The first inlet tube 121 and the second inlet tube 122 may have respective inner diameters D1 and D2 such that the cross-sectional areas of the first inlet lumen 131 and the second inlet lumen 132 are less than the cross-sectional area of the internal chamber 110.

The sliding valve member 200 includes a body 201, a first sealing end 202, and a second sealing end 203. In one example, the first sealing end 202 and the second sealing end 203 may be frustoconical or hemispherical in shape and are axially aligned with the first inlet lumen 131 and the second inlet lumen 132, respectively. Base diameters D3 and D4 of the first sealing end 202 and the second sealing end 203 may be larger than the inner diameters D1 and D2 of the first inlet lumen 131 and the second inlet lumen 132, respectively. According to these embodiments, the first sealing end 202 and the second sealing end 203 cannot entirely enter the first inlet lumen 131 and the second inlet lumen 132, respectively. In various embodiments, the sliding valve member 200 has at least one channel 211 (FIG. 8) that allows pressurized fluid within the internal chamber 110 to flow around the exterior surface of the sliding valve member 200 and flow out of the outlet lumen 133 of the outlet tube 123. According to certain embodiments, at least one of the sealing ends 202 and 203 and/or the distal ends of the first and second lumens 131 and 132 may be made of a pliable material so that when the sealing end abuts the distal end of the lumen under pressure, a fluid tight seal is formed.

With continued reference to FIGS. 6A-C, the sliding valve member 200 freely slides within the internal chamber 110 between three operating states based on the relative differential of pressures and/or flow rates in the first inlet lumen 131 and the second inlet lumen 132. In a first operating state shown in FIG. 6A where the fluid pressure and/or flow rate through the second inlet lumen 132 is significantly greater than the fluid pressure and/or flow rate through the first inlet lumen 131, for example when the first syringe 30a is inactive and the second syringe 30b is actively pressurized, the sliding valve member 200 is forced toward the first inlet tube 121 such that the first sealing end 202 of the sliding valve member 200 is engaged with the first inlet tube 121, thereby preventing fluid communication between the internal chamber 110 and the first inlet lumen 131 and preventing flow into or out of the first inlet lumen 131. Movement of the sliding valve member 200 is caused by the drag coefficient of the sliding valve member 200 in response to the fluid flow from the second inlet lumen 132. With the sliding valve member 200 moved toward the first inlet lumen 131, fluid flow of the second fluid is directed around an outer surface of the sliding valve member 200 via the at least one channel 211 and through the outlet lumen 133.

In a second operating state shown in FIG. 6B where the fluid pressure and/or flow rate through the first inlet lumen 131 is significantly greater than the fluid pressure and/or flow rate through the second inlet lumen 132, for example when the first syringe 30a is actively pressurized and the second syringe 30b is inactive, the sliding valve member 200 is forced toward the second inlet tube 122 such that the second sealing end 203 of the sliding valve member 200 is engaged with the second inlet tube 122, thereby preventing fluid communication between the internal chamber 110 and the second inlet lumen 132 and preventing flow into or out of the second inlet lumen 132. Movement of the sliding valve member 200 is caused by the drag coefficient of the sliding valve member 200 in response to the fluid flow from the first inlet lumen 131. With the sliding valve member 200 moved toward the second inlet lumen 132, fluid flow of the first fluid is directed around an outer surface of the sliding valve member 200 via the at least one channel 211 and through the outlet lumen 133.

In a third operating state shown in FIG. 6C where the fluid pressure and/or flow rate through the second inlet lumen 132 and the fluid pressure and/or flow rate through the first inlet lumen 131 are substantially similar, i.e., a small pressure and/or flow rate differential, the sliding valve member 200 remains in the internal chamber 110 and is not engaged with either the first inlet tube 121 or the second inlet tube 122. Rather, the drag coefficient created by fluid flow from the first inlet lumen 131 is equal to the drag coefficient created by fluid flow from the second inlet lumen 132, preventing the sliding valve member 200 from moving in either direction. Both the first fluid out of the first inlet lumen 131 and the second fluid out of the second inlet lumen 132 flow around an outer surface of the sliding valve member 200, via the at least one channel 211, and through the outlet lumen 133. As the first fluid and the second fluid meet at the outlet lumen 133, turbulent mixing of the fluids may occur to provide a uniform mixture of the first and second fluids.

With reference to FIG. 7, in another example, the first sealing end 202 and the second sealing end 203 may be hemispherical in shape and axially aligned with the first inlet lumen 131 and the second inlet lumen 132, respectively. The base diameters D3 and D4 of the first sealing end 202 and the second sealing end 203 may be larger than the inner diameters D1 and D2 of the first inlet lumen 131 and the second inlet lumen 132, respectively. As such, the first sealing end 202 and the second sealing end 203 cannot entirely enter the first inlet lumen 131 and the second inlet lumen 132, respectively. Other possible shapes for the first sealing end 202 and second sealing end 203, such as conical, ovaline, or parabolic, may also be appreciated by one having skill in the art.

Figure 8:
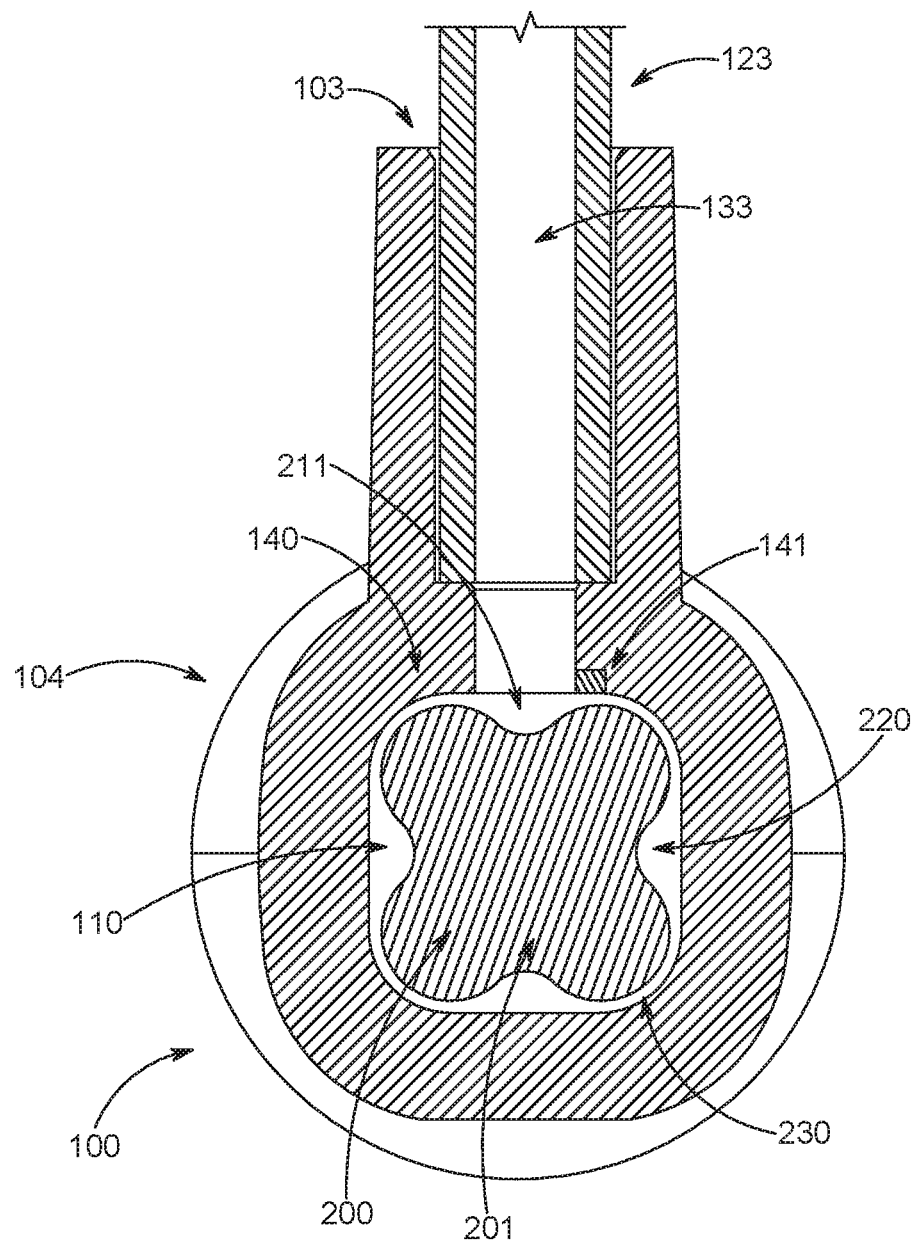
FIG. 8 is a side sectional view of the fluid control valve of FIGS. 6A-6C.

With reference to FIG. 8, the sliding valve member 200 may have a cross-sectional profile 220 which engages the internal chamber 110 to prevent the sliding valve member 200 from rotating within the internal chamber 110. The sliding valve member 200 and the valve body 104 define at least one channel 211 in fluid communication with the outlet lumen 133 such that fluid may flow through the at least one channel 211 and into the outlet lumen 133. In the first operating state (shown in FIG. 6A), the at least one channel 211 is in fluid communication with both the second inlet lumen 132 and the outlet lumen 133 but isolated from the first inlet lumen 131. In the second operating state (shown in FIG. 6B), the at least one channel 211 is in fluid communication with both the first inlet lumen 131 and the outlet lumen 133, but isolated from the second inlet lumen 132. In the third operating state (shown in FIG. 6C), the at least one channel is in fluid communication with the first inlet lumen 131, the second inlet lumen 132, and the outlet lumen 133. The sliding valve member 200 may have any suitable cross-sectional profile 220 along with a corresponding complimentary profile of the internal chamber 110 to allow the sliding valve member 200 to freely travel laterally within the internal chamber 110 without rotation. In certain embodiments, the sliding valve member 200 may have a substantially polygonal cross section with a corresponding complimentary internal chamber profile.

With continued reference to FIG. 8, in one example, a top end or surface 140 of the internal chamber 110 associated with the outlet port 103 may be flat, creating a right angle step 141 between the internal chamber 110 and the outlet port 103. This may be beneficial for manufacturing the fluid control valve 100, because the right angle step 141 may be formed using a flat-topped mold pin for the internal chamber 110 with a cylindrical mold pin for the outlet port 103. The interface between the flat top of the internal chamber mold pin and bottom of the outlet port mold pin is flush, which would not be the case if the internal chamber 110 had a rounded top. The flush mold pin interface eliminates the formation of "flashing", or excess injection material which can form at an interface of mold pieces which are not flush with one another. "Flashing" would be undesirable between the internal chamber 110 and the outlet port 103 because it could obstruct fluid flow through the outlet port 103 and/or impede the free movement of the sliding valve member 200 within the internal chamber 110.

With continued reference to FIG. 8, the cross section of the internal chamber 110 need not be any particular shape and need not be symmetrical, so long as the cross section of the internal chamber 110 corresponds approximately to the cross-sectional profile 220 of the sliding valve member 200. In accordance with one example, the cross section of the internal chamber may be generally rectilinear with filleted corners to prevent the sliding valve member 200 from rotating within the internal chamber. The cross section of the internal chamber 110 may further include a clearance gap 230 between the perimeter of the internal chamber 110 and the cross-sectional profile 220 of the sliding valve member 200 to prevent the sliding valve member 200 from becoming lodged in the internal chamber 110.

Figure 9:
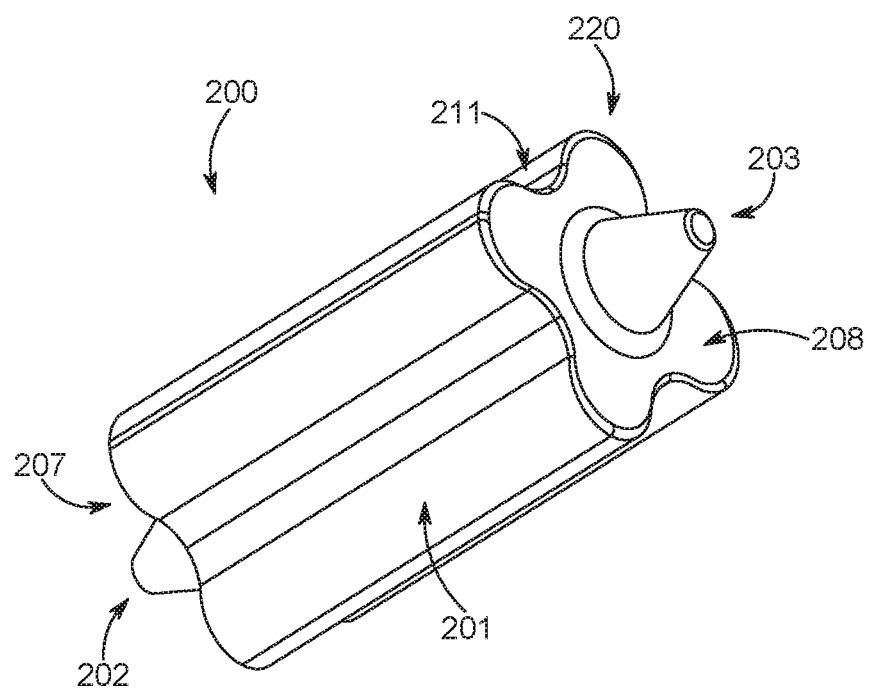
FIG. 9 is a perspective view of a sliding valve member of the fluid control valve of FIGS. 6A-8.

With reference to FIG. 9, some examples of the sliding valve member 200 include a first pressure face 207 and a second pressure face 208 associated with the first inlet lumen 131 and the second inlet lumen 132, respectively. The first pressure face 207 and the second pressure face 208 are perpendicular to the first inlet lumen 131 and the second inlet lumen 132, respectively, such that fluid flow and drag force imparted on the first pressure face 207 induces the sliding valve member 200 to translate axially away from the first inlet lumen 131, and fluid flow and drag force imparted on the second pressure face 208 induces the sliding valve member 200 to translate axially away from the second inlet lumen 132.

In operation, the fluid control valve 100 isolates the first syringe 30a or the second syringe 30b based on the relative pressure differential between the fluid pressure in the first syringe 30a and the fluid pressure in the second syringe 30b. For example, the fluid pressure in the first syringe 30a may exceed the fluid pressure in the second syringe 30b. In this instance, the high pressure fluid from the first syringe 30a passes through the first inlet lumen 131, into the internal chamber 110, and engages the first pressure face 207 of the sliding valve member 200. The fluid flow and resulting drag coefficient on the first pressure face 207 causes the sliding valve member 200 to slide away from the first inlet lumen 131 until the second sealing end 203 engages and seats at the second inlet tube 122, coming to rest in the second operating state as shown in FIG. 6B. Once the second sealing end 203 has engaged the second inlet tube 122, the second inlet lumen 132 is isolated from the fluid delivery system and the capacitance of all components upstream of the second inlet port 102 is removed from the fluid delivery system. Fluid from the first inlet lumen 131 may flow into the internal chamber 110 and through the at least one channel 211 to the outlet port 103.

Similarly, if the fluid flow rate and the resulting drag coefficient from the second syringe 30b is higher than the fluid flow rate and the resulting drag coefficient from the first syringe 30a, the sliding valve member 200 slides away from the high flow of the second input lumen 132, and the first sealing end 202 engages and seats at the first inlet tube 121. The first inlet lumen 131 is thus isolated from the fluid delivery system, as shown in FIG. 6A, and the capacitance of all components upstream of the second inlet port 102 is removed from the fluid delivery system. Fluid from the second inlet lumen 132 may flow into the internal chamber 110 and through the at least one channel 211 to the outlet port 103.

If there is little or no pressure and/or flow differential between the first inlet lumen 131 and the second inlet lumen 132, for example, when the fluid pressures of the first and second fluids are substantially equal, the sliding valve member 200 may balance in the internal chamber 110 such that the sliding valve member 200 is not engaged with either the first inlet tube 121 or the second inlet tube 122, as shown in FIG. 6C. In this dual-flow configuration, fluid from both the first inlet lumen 131 and the second inlet lumen 132 may pass through the at least one channel 211 and into the outlet port 103.

Figure 10A:
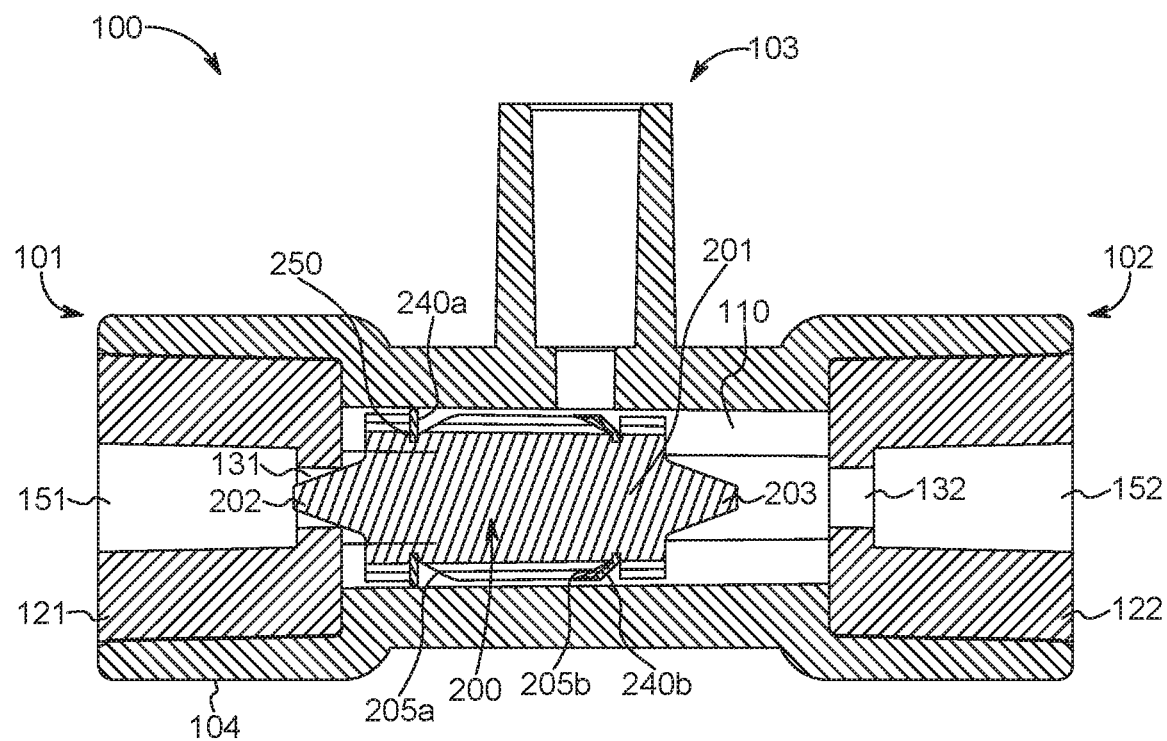
FIG. 10A is a front sectional view of the fluid control valve and a sliding valve member according to another example of the present disclosure, with the sliding valve member shown in the first operating state.
Figure 10B:
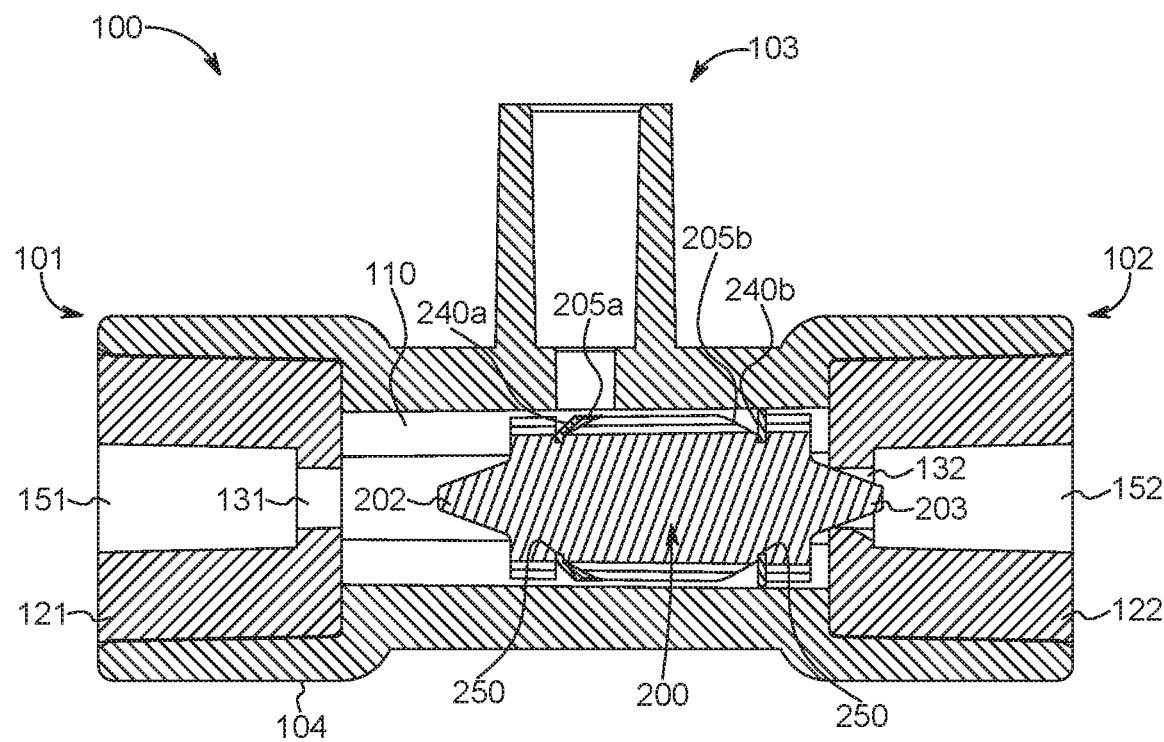
FIG. 10B is a front sectional view of the fluid control valve of FIG. 10A with a sliding valve member shown in the second operating state.
Figure 10C:
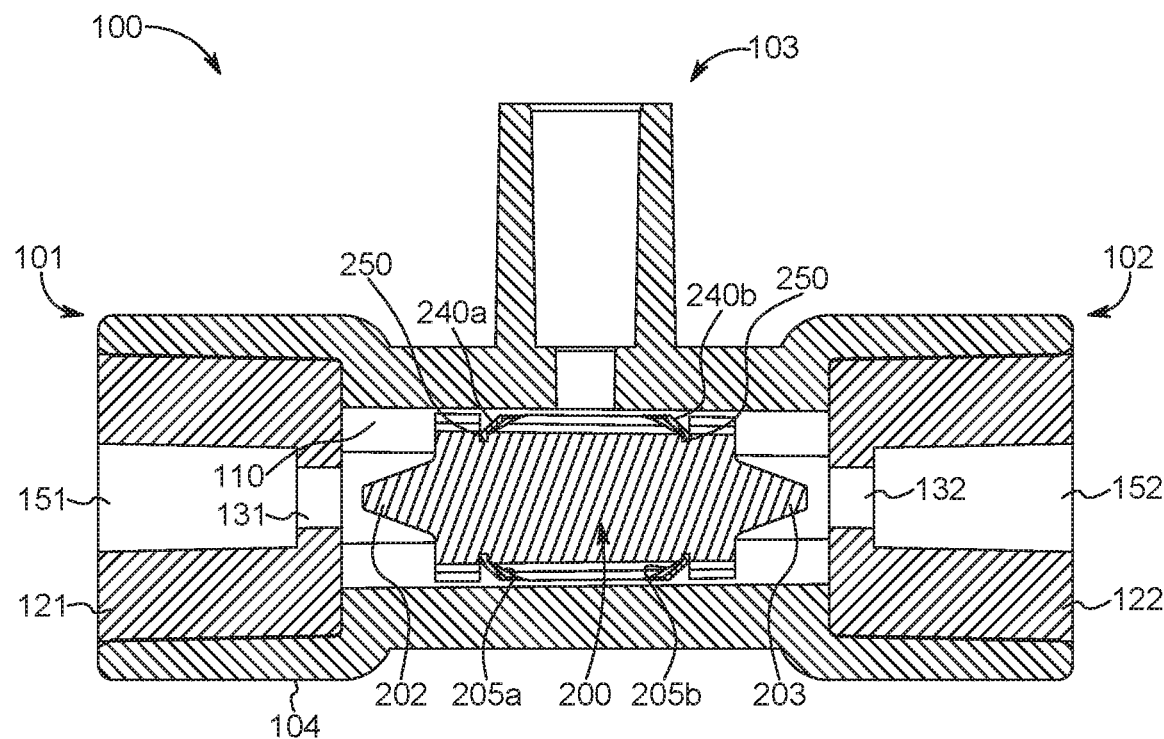
FIG. 10C is a front sectional view of the fluid control valve of FIG. 10A with a sliding valve member shown in the third operating state.
Figure 11:
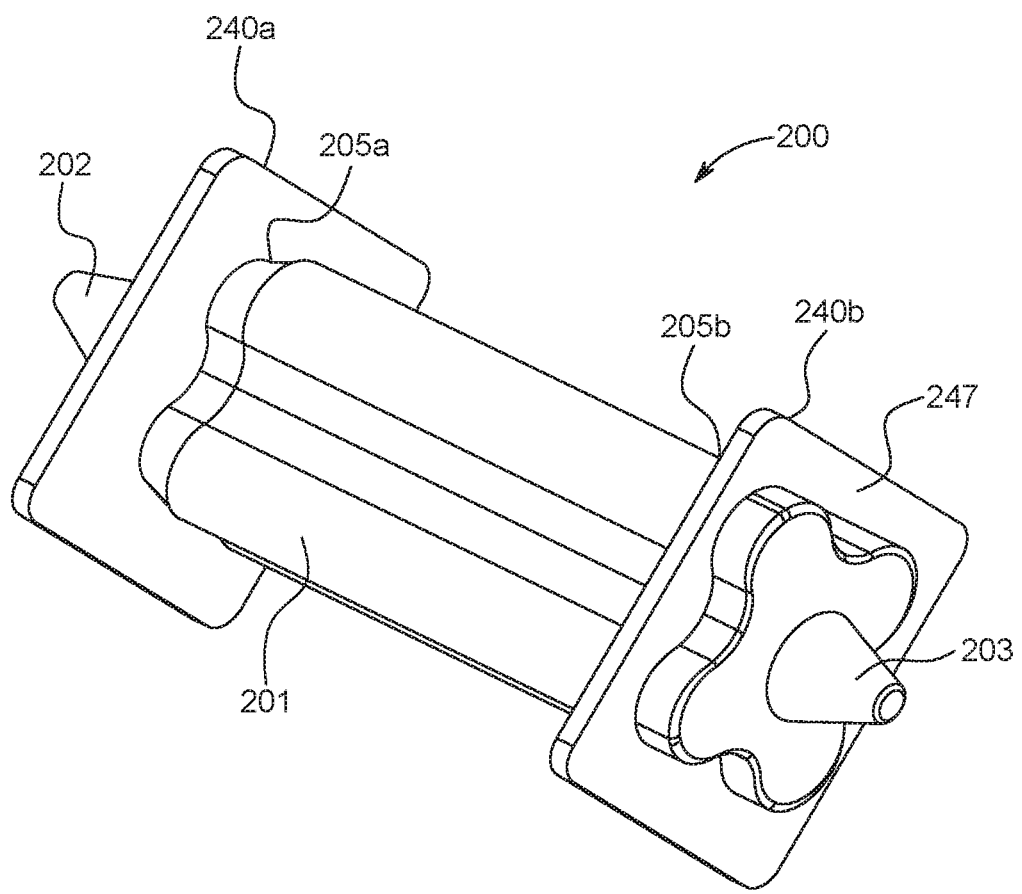
FIG. 11 is a perspective view of the sliding valve member of the fluid control valve of FIGS. 10A-10C.
Figure 12:
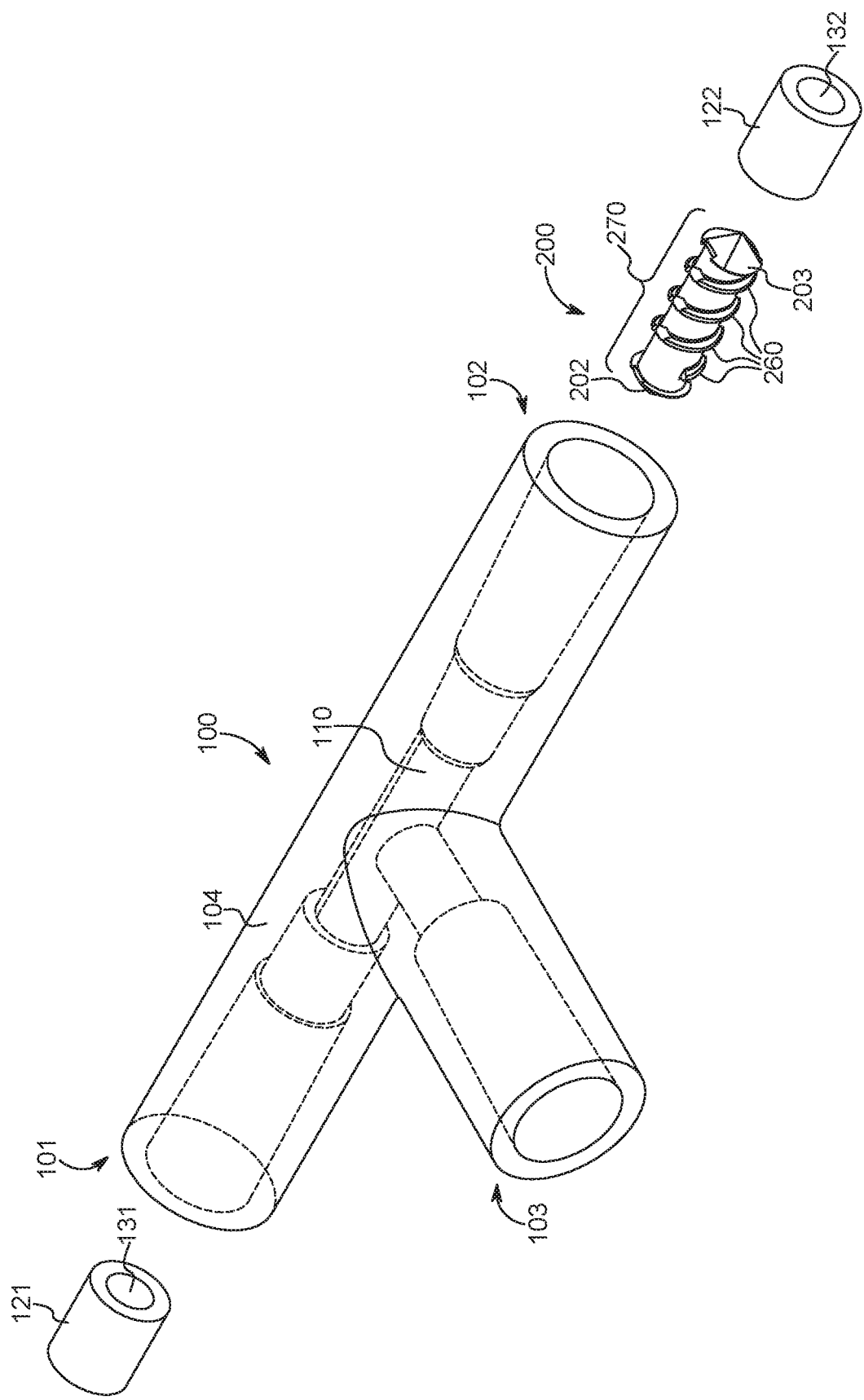
FIG. 12 is an exploded view of another example of a fluid control valve according to the present disclosure.
Figure 13:
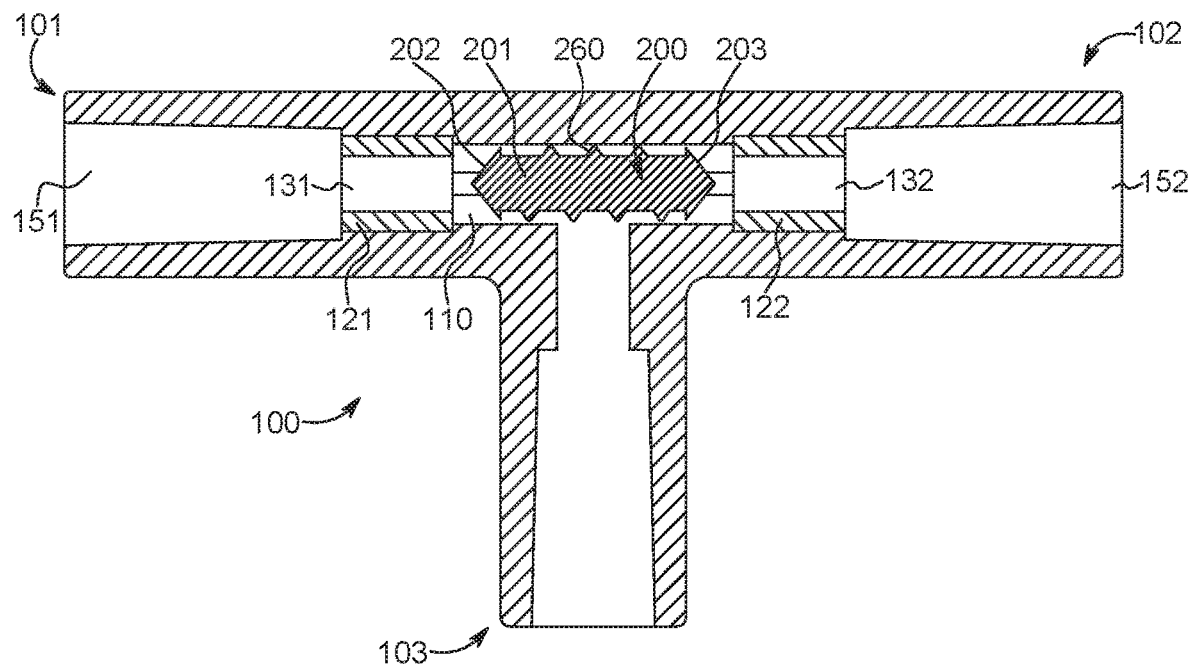
FIG. 13 is a front sectional view of the fluid control valve of FIG. 12.

FIGS. 10A-11 depict another example of the fluid control valve 100 and the sliding valve member 200 which may be substantially similar to the fluid control valve 100 and the sliding valve member 200 depicted in FIGS. 4-9. As such, only the differences in the fluid control valve 100 and the sliding valve member 200 of FIGS. 10A-11 will be discussed in detail. Referring to FIGS. 10A-10C, in some examples, the first inlet tube 121 may be an adapter having a first connecting lumen 151 configured to receive external tubing (not shown). Similarly, the second inlet tube 122 may be an adapter having a second connecting lumen 152 configured to receive external tubing (not shown). The external tubing may be in fluid connection with the end caps 37a, 37b of the syringes 30a, 30b. In such examples, the first inlet tube 121 and second inlet tube 122 constrain the sliding valve member within the valve body 104, without external tubing being attached. The first inlet tube 121 and the second inlet tube 122 may be secured in place, for example by an adhesive, welding, solvent bonding, or laser welding process.

As may be appreciated from FIG. 11, the sliding valve member 200 may include opposing flange members 240a, 240b extending radially from the body 201 of the sliding valve member 200. A front surface 247 of each flange member 240 works in tandem with the first and second pressure faces 207, 208 to increase the exposed surface area of the first and second pressure faces 207, 208, thereby increasing the drag coefficient of the sliding valve member 200, to induce axial translation of the sliding valve member 200 when fluid flow is applied to the front surface 247. The flange members 240 may be made of a resilient material such that each flange member 240 deflects in a direction of the longitudinal axis of the sliding valve member 200 when sufficient fluid pressure is applied to the front surface 247 of the flange member 240. To accommodate deflection of the flange members 240, one or more relief sections 205 may be formed into the body 201 of the sliding valve member 200 adjacent to flange members 240 in the direction of deflection of the flange members 240. As shown in FIGS. 10A-11, the flange members 240 may be disposed in respective grooves 250 formed around the circumference of the body 201 of the sliding valve member 200. In other examples, the flange members 240 may be integrally formed with the body 201 of the sliding valve member 200. Flange members 240 may be configured to substantially decrease the clearance gap 230 between the sliding valve member 200 and the perimeter of the internal chamber 110 to minimize fluid flow around the sliding valve member 200 until a deflection pressure or flow force threshold is reached, while still allowing the sliding valve member 200 to freely slide within the internal chamber 110.

The fluid flow sufficient to deflect the flange member 240 from an undeflected state to a deflected state (hereinafter the "deflection flow force") is a function of the material stiffness of the flange member 240, the thickness of the flange member 240, the radial length from the perimeter of the body 201 to the perimeter of the flange member 240, and the surface area of the front surface 247. As such, the flange members 240 may be specifically designed to deflect at a predetermined deflection flow threshold by changing any of the factors governing the deflection characteristics of the flange members 240.

In some examples, the cross-sectional shape of the flange members 240, when in the undeflected state, is substantially identical to the cross-sectional shape of the internal chamber 110 of the fluid control valve 100 such that the flange members 240 form a seal against the internal chamber 110. As such, fluid is prevented from flowing around the flange member 240 and through the internal chamber 110 when the flange member 240 is in the undeflected state. Once the fluid flow reaches the deflection flow force threshold of the flange member 240, the flange member 240 deflects to the deflected state such that fluid may pass around the flange member 240.

Referring again to FIGS. 10A-10C, various operating states of the fluid control valve 100 are based on the flow differential between the first inlet lumen 131 and the second inlet lumen 132, similar to the first operating state, the second operating state, and the third operating state discussed with reference to FIGS. 6A-6C. In each of FIGS. 10A-10C, the flange members 240 include a first flange member 240a associated with the fluid entering the fluid control valve 100 from the first inlet lumen 131 and a second flange member 240b associated with the fluid entering the fluid control valve 100 from the second inlet lumen 132. FIG. 10A shows the fluid control valve 100 and the sliding valve member 200 in the first operating state, in which the fluid pressure in the second inlet lumen 132 exceeds the fluid pressure in the first inlet lumen 131, and the fluid pressure in the second inlet lumen 132 equals or exceeds the deflection flow force of the second flange member 240b. Thus, the second flange member 240b is deflected away from the second inlet lumen 132 and into a second relief 205b such that fluid from the second inlet lumen 132 is allowed to pass around the second flange member 240b in the internal chamber 110 and to the outlet lumen 133. Under the pressure differential, the first flange member 240a is forced toward the groove surface 250 opposite the first relief 205a, increasing the seal between the sliding valve member 200 and the first inlet lumen 131.

FIG. 10B shows the fluid control valve 100 and the sliding valve member 200 in the second operating state, in which the fluid pressure in the first inlet lumen 131 exceeds the fluid pressure in the second inlet lumen 132, and the fluid pressure in the first inlet lumen 131 equals or exceeds the deflection flow force of the first flange member 240a. Thus, the first flange member 240a is deflected away from the first inlet lumen 131 and into the first relief 205a such that fluid from the first inlet lumen 131 is allowed to pass around the first flange member 240a in the internal chamber 110 and to the outlet lumen 133. Under the pressure differential, the second flange member 240b is forced toward the groove surface 250 opposite the second relief 205b, increasing the seal between the sliding valve member 200 and the second inlet lumen 132.

FIG. 10C shows the fluid control valve 100 and the sliding valve member 200 in the third operating state, in which the fluid flow and resulting drag coefficient from the first inlet lumen 131 and the second inlet lumen 132 are substantially the same, and therefore no flow force differential—or a negligible flow force differential—exists between fluid in the first inlet lumen 131 and fluid in the second inlet lumen 132. Thus, as discussed above in reference to FIG. 6C, the sliding valve member is balanced in the internal chamber 110 such that the sliding valve member 200 is not engaged with either the first inlet tube 121 or the second inlet tube 122. In FIG. 10C, the fluid flow at each of the first inlet lumen 131 and the second inlet lumen 132 equals or exceeds the deflection flow force threshold of the associated flange members 240a, 240b, and the first and second flange members 240a, 240b are deflected away from the first inlet lumen 131 and the second inlet lumen 132 and into the first relief 205a, and the second relief 205b, respectively. As both flange members 240a, 240b are in the deflected state, the first fluid from the first inlet lumen 131 and the second fluid from the second inlet lumen 132 are allowed to pass around the flange members 240a, 240b in the internal chamber 110 and to the outlet lumen 133.

FIGS. 12-15 show other aspects of the fluid control valve 100 and the sliding valve member 200. Only the differences between the fluid control valve 100 and the sliding valve member 200 of FIGS. 12-15 and the fluid control valve 100 and the sliding valve member 200 of the previously-described examples will be discussed. As may be appreciated from FIGS. 12-13, the first inlet tube 121 and the second inlet tube 122 may be collars insertable into the valve body 104 to abut the first shoulder 106 and second shoulder 107, respectively. The first inlet tube 121 and the second inlet tube 122 may be secured in place, for example by an adhesive, welding, solvent bonding, or laser welding process. External tubing (not shown) may be inserted into the first inlet port 101 and second inlet port 102 after insertion of the first inlet tube 121 and the second inlet tube 122. The external tubing may be in fluid connection with the end caps 37a, 37b of the syringes 30a, 30b. Like the example of FIGS. 10A-10C, the first inlet tube 121 and the second inlet tube 122 may constrain the sliding valve member within the valve body 104, without external tubing being attached.

The sliding valve member 200 may include one or more mixing features, such a turbulent flow mixing feature, for example one or more helical ridges 260 wrapping around the body 201 of the sliding valve member 200. When disposed in the internal chamber 110 of the fluid control valve 100, the helical ridge 260 defines helical channels for fluid flow entering the internal chamber 110. In the third operating state, in which a first fluid from the first inlet lumen 131 and a second fluid from the second inlet lumen 132 both enter the internal chamber 110, the flow of the fluids induced by the helical ridge 260 causes turbulent mixing at the confluence of the first and second fluids as the fluids flow toward and out of the outlet lumen 133. Thus, fluid exiting the fluid control valve 100 toward the patient is of a consistent and uniform mixture desired for an injection protocol. In some examples, additional turbulent flow mixing features may be provided in the housing 104 of the fluid control valve 100 or in the outlet lumen 133. Examples of suitable flow mixing features may be found in U.S. Pat. No. 9,555,379, the disclosure of which is incorporated herein by reference in its entirety.

Figure 14:
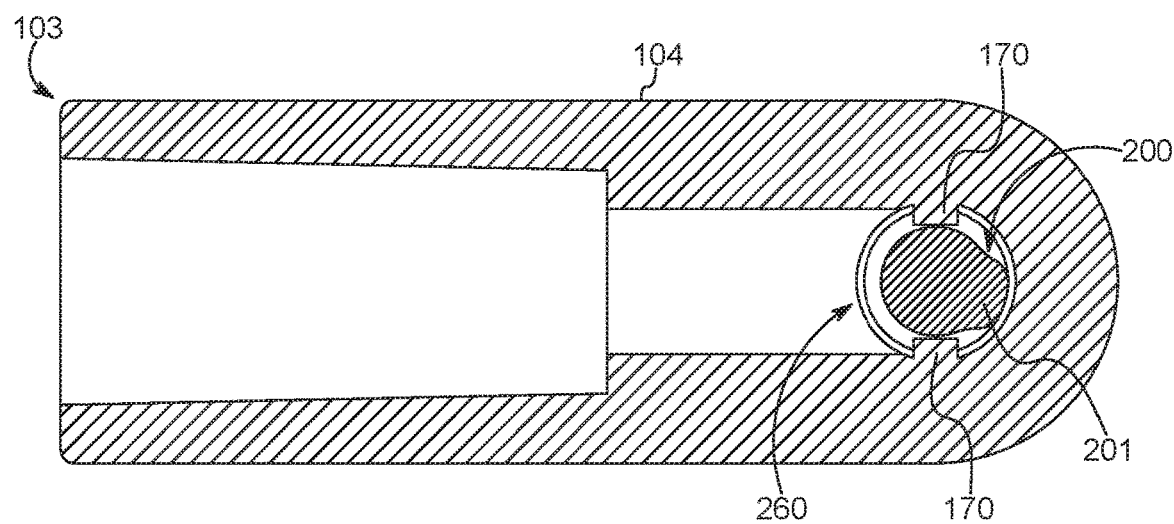
FIG. 14 is a side sectional view of the fluid control valve of FIG. 12.
Figure 15:
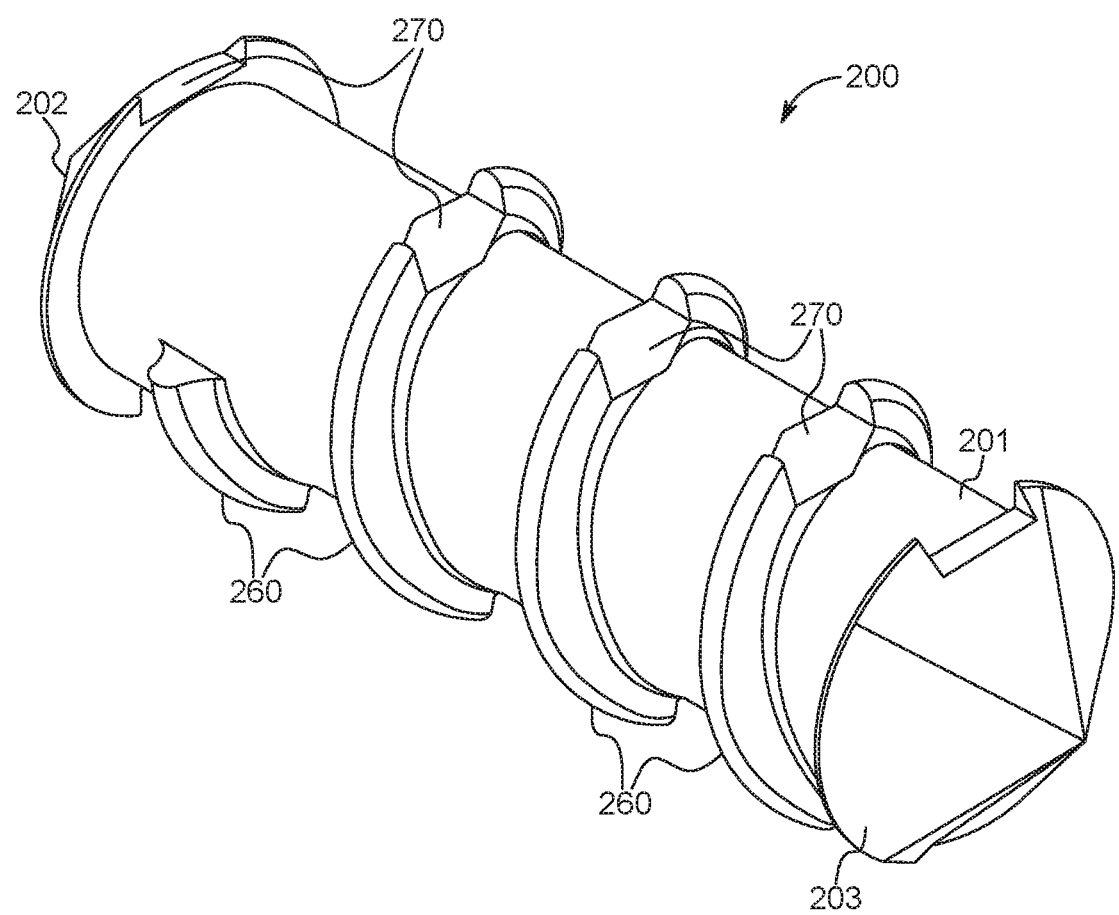
FIG. 15 is a perspective view of the sliding valve member of the fluid control valve of FIGS. 12-14.

As shown in FIGS. 14-15, the sliding valve member 200 may be prevented from rotating within the internal chamber 110 by one or more rotation stop ridges 170 formed on the valve body 104 and corresponding to one or more rotation stop grooves 270 formed in the sliding valve member 200. The interaction of the one or more rotation stop ridges 170 and the one or more rotation stop grooves 270 allows the sliding valve member 200 to move linearly parallel to the longitudinal axis of the sliding valve member 200, but prohibits rotation of the sliding valve member 200 about the longitudinal axis thereof, for example as pressurized fluid flows over the helical ridge 260. In other examples, rotation stop ridges may be formed on the sliding valve member 200 and rotation stop grooves may be formed in the internal chamber 110.

Figure 16:
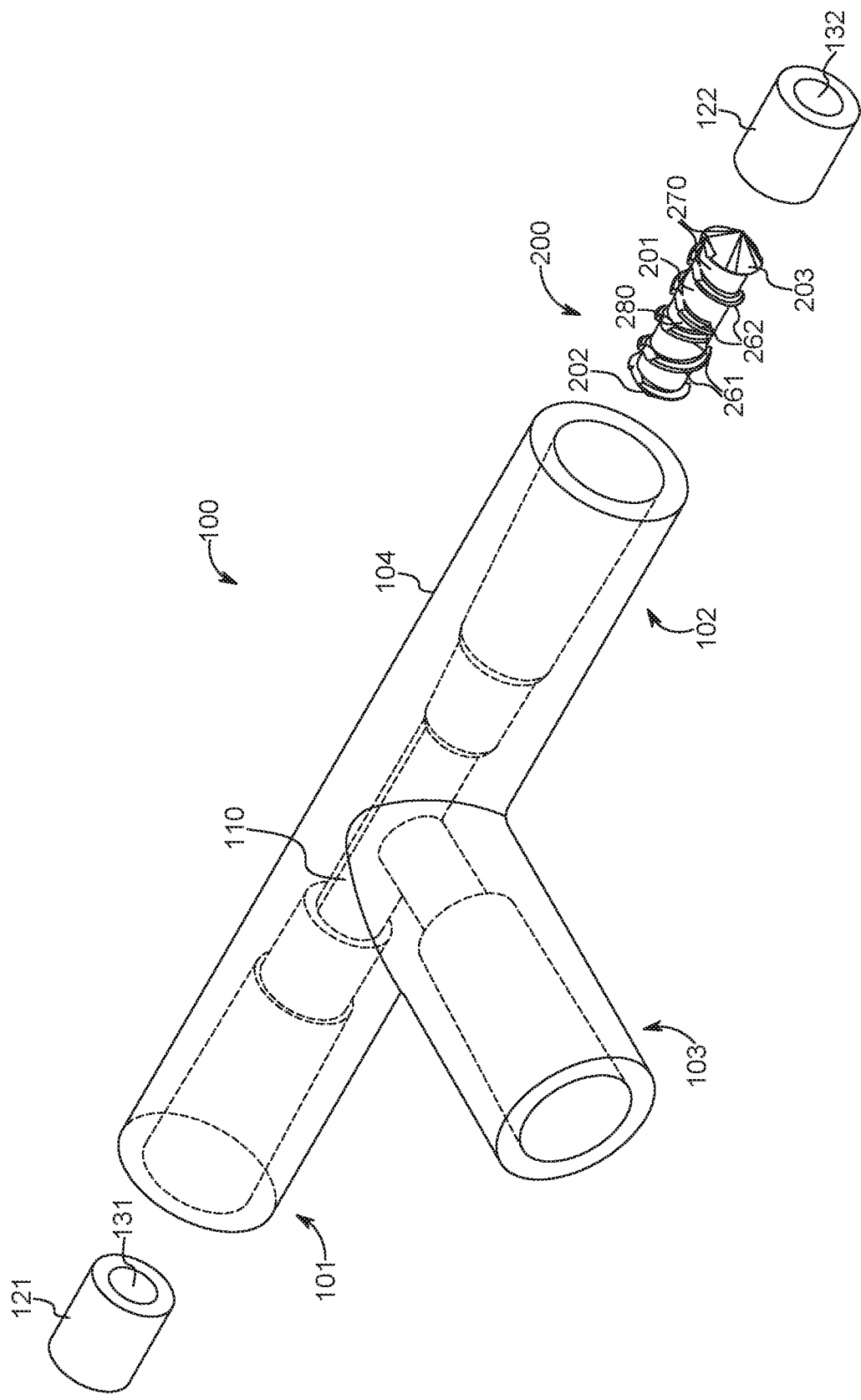
FIG. 16 is an exploded view of another example of a fluid control valve according to the present disclosure.
Figure 17:
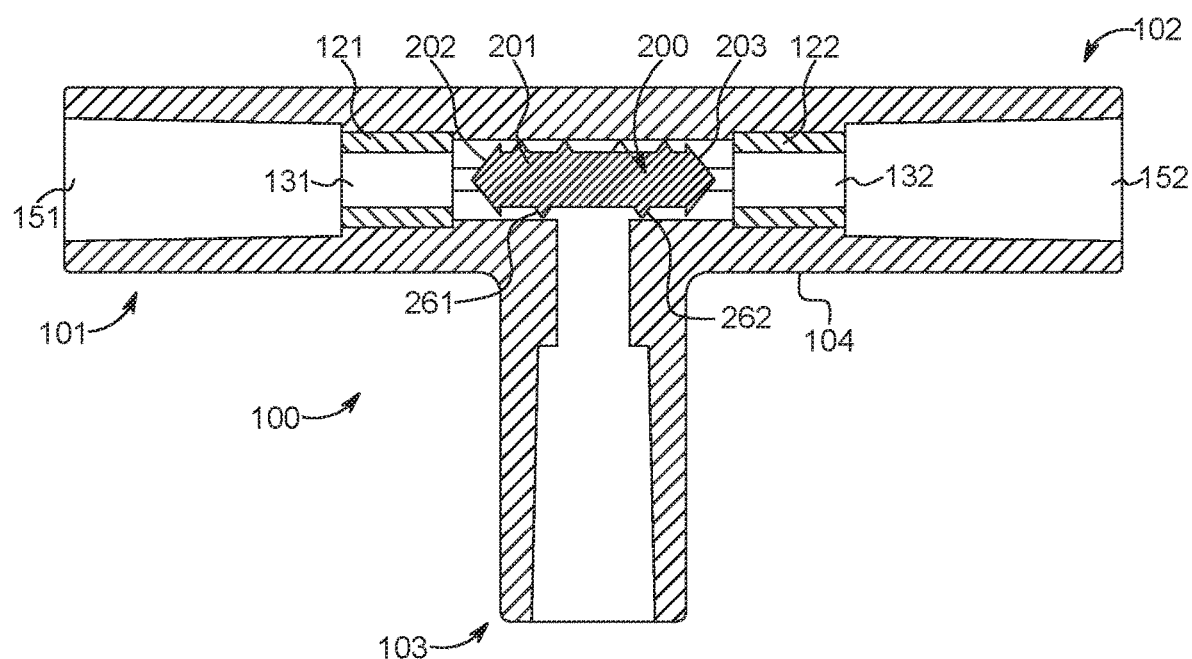
FIG. 17 is a front sectional view of the fluid control valve of FIG. 16.
Figure 18:
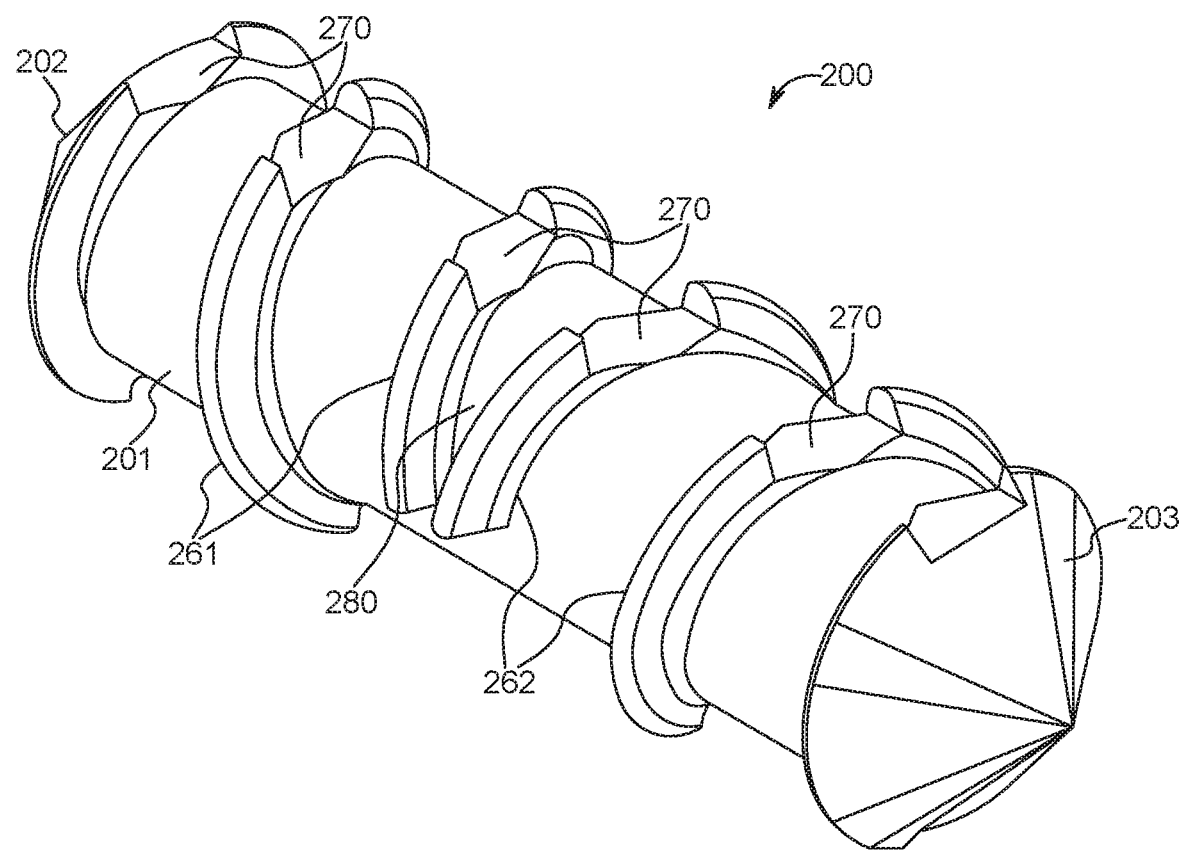
FIG. 18 is a perspective view of the sliding valve member of the fluid control valve of FIGS. 16-17.
Figure 19:
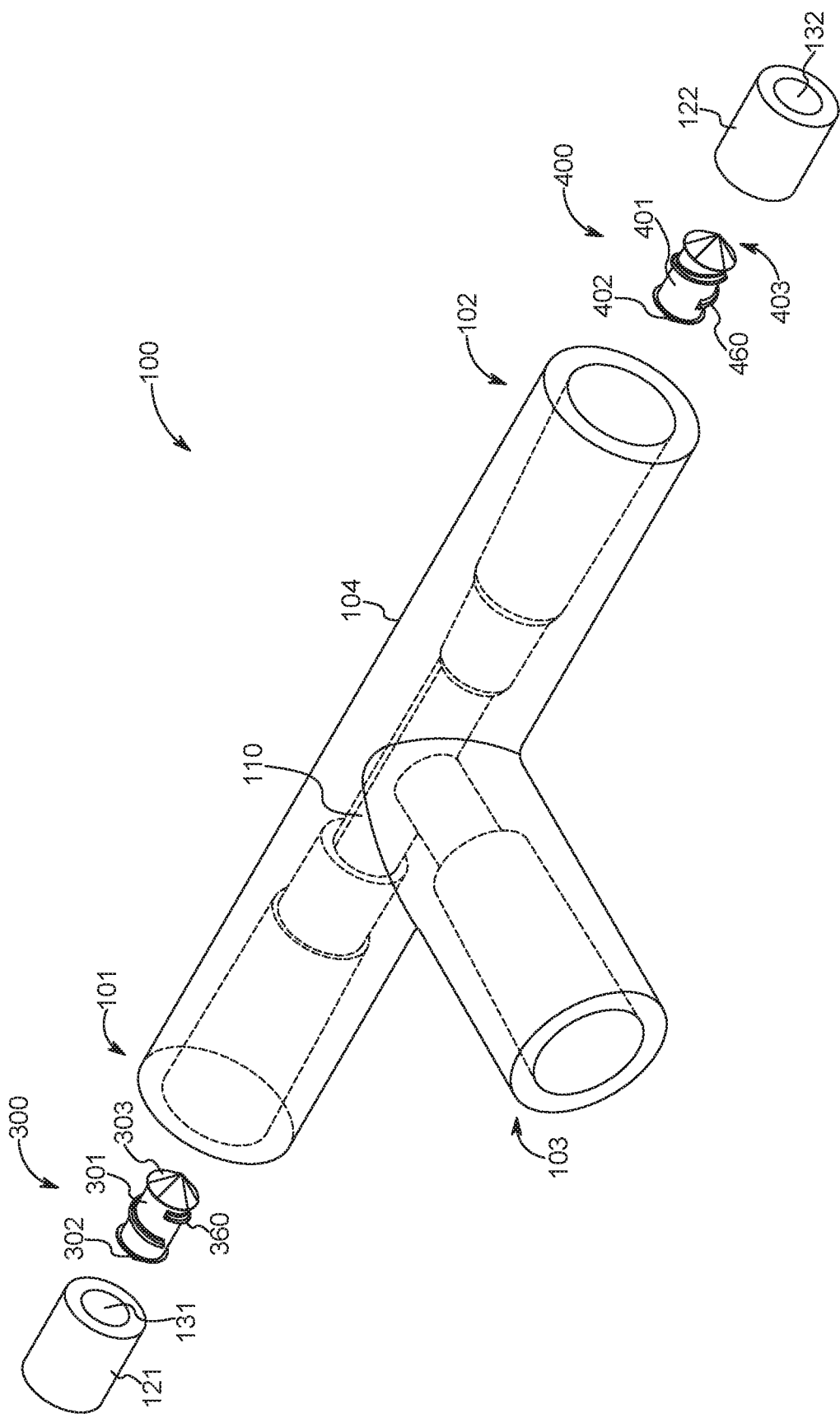
FIG. 19 is an exploded view of another example of a fluid control valve according to the present disclosure.

FIGS. 16-18 depict other aspects of the sliding valve member 200 substantially similar to the example of FIGS. 12-15, except that the mixing features include a first helical ridge 261 and a second helical ridge 262 having opposite directionality. According to these examples, when in the third operating state during a dual-flow injection portion of an injection protocol, in which fluid from the first inlet lumen 131 and the second inlet lumen 132 both enter the internal chamber 110, turbulent mixing of the fluids occurs at a mixing point 280 defined by the intersection of the first and second helical ridges 261, 262 as the first and second fluids flow in helical opposite directions around the helical ridges 261 and 262, and turbulently mix at the mixing point 280 and then the mixture of the first and second fluids flows toward and out of the outlet lumen 133.

FIGS. 19-23 depict other aspects of the fluid control valve 100 and the sliding valve member 200 substantially similar to that of FIGS. 16-18, except that the sliding valve member 200 includes at least two parts—a first part sliding valve member 300 and a second part sliding valve member 400. The first part sliding valve member 300 may include a body 301, a first sealing end 302, a second end 303, a helical ridge 360, and one or more rotation stop grooves 370. The second part sliding valve member 400 may include a body 401, a first sealing end 403, a second end 402, a helical ridge 460, and one or more rotation stop grooves 470. The helical ridge 360 of the first part sliding valve member 300 may have the same directionality or opposite directionality as the helical ridge 460 of the second part sliding valve member 400.

The valve body 104 of the fluid control valve 100 may include a partition 180 projecting into the internal chamber 110 and providing a mechanical stop for the first part sliding valve member 300 and the second part sliding valve member 400. The first part sliding valve member 300 is freely slidable between the first inlet tube 121 and the partition 180. The second part sliding valve member 400 is freely slidable between the second inlet tube 122 and the partition 180.

Figure 20A:
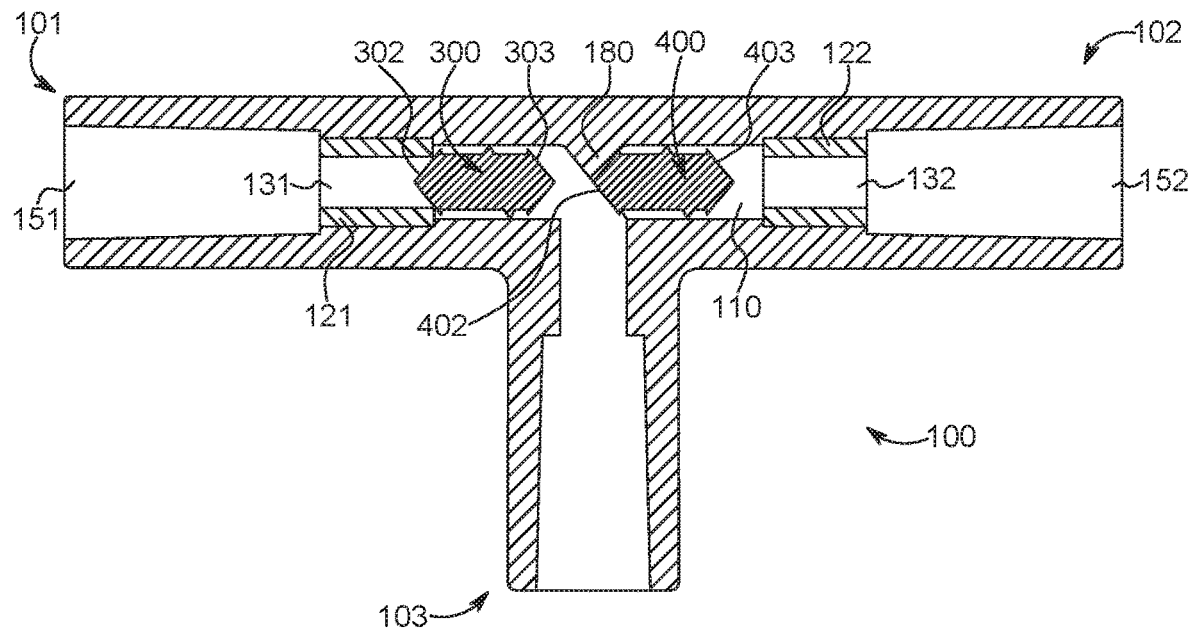
FIG. 20A is a front sectional view of the fluid control valve and sliding valve member according to another example of the present disclosure, with the sliding valve member shown in the first operating state.

As shown in FIG. 20A, in the first operating state where the fluid flow and resulting drag coefficient through the second inlet lumen 132 is greater than the fluid flow and resulting drag coefficient through the first inlet lumen 131, the first sealing end 302 of the first part sliding valve member 300 is engaged with the first inlet tube 121, thereby preventing flow into or out of the first inlet lumen 131. The second end 402 of the second part sliding valve member 400 engages the partition 180. Fluid flow from the second inlet lumen 132 is directed around the helical ridge 460 of the second part sliding valve member 400 and through the outlet lumen 133.

Figure 20B:
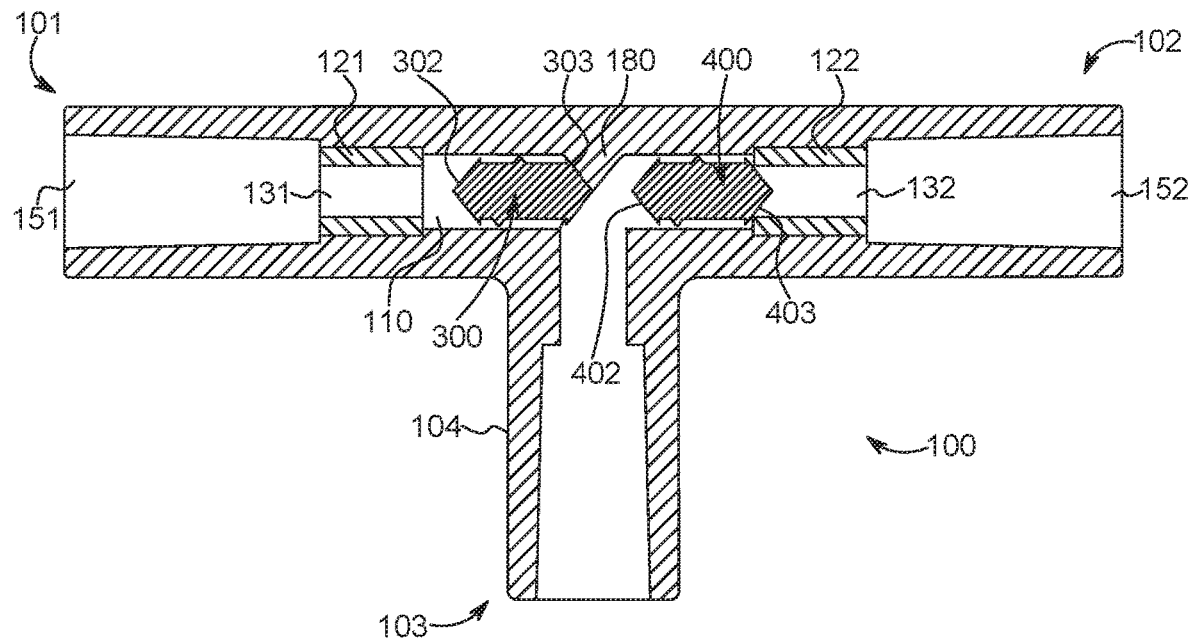
FIG. 20B is a front sectional view of the fluid control valve of FIG. 20A with sliding valve member shown in the second operating state.

In a second operating state shown in FIG. 20B where the fluid flow and resulting drag coefficient through the first inlet lumen 131 is greater than the fluid flow and resulting drag coefficient through the second inlet lumen 132, the first sealing end 403 of the second part sliding valve member 400 is engaged with the second inlet tube 122, thereby preventing flow into or out of the second inlet lumen 132. The second end 303 of the first part sliding valve member 300 engages the partition 180. Fluid flow from the first inlet lumen 131 is directed around the helical ridge 360 of the first part sliding valve member 300 and through the outlet lumen 133.

Figure 20C:
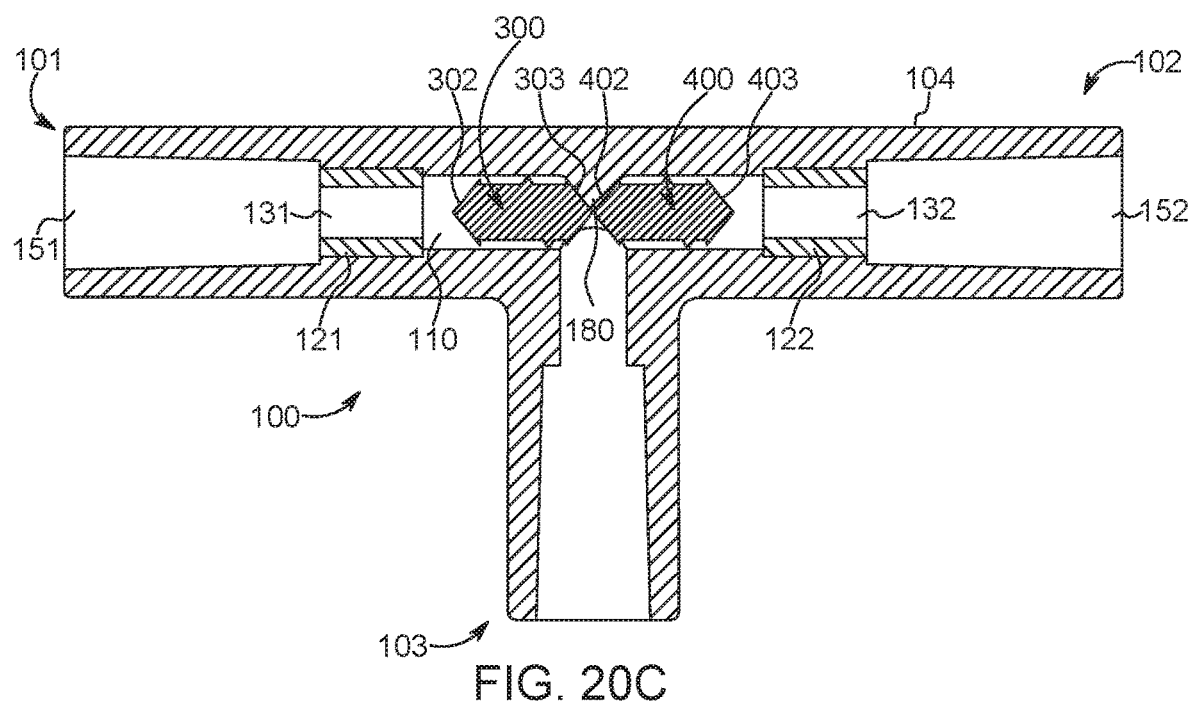
FIG. 20C is a front sectional view of the fluid control valve of FIG. 20A with sliding valve member shown in the third operating state.
Figure 21:
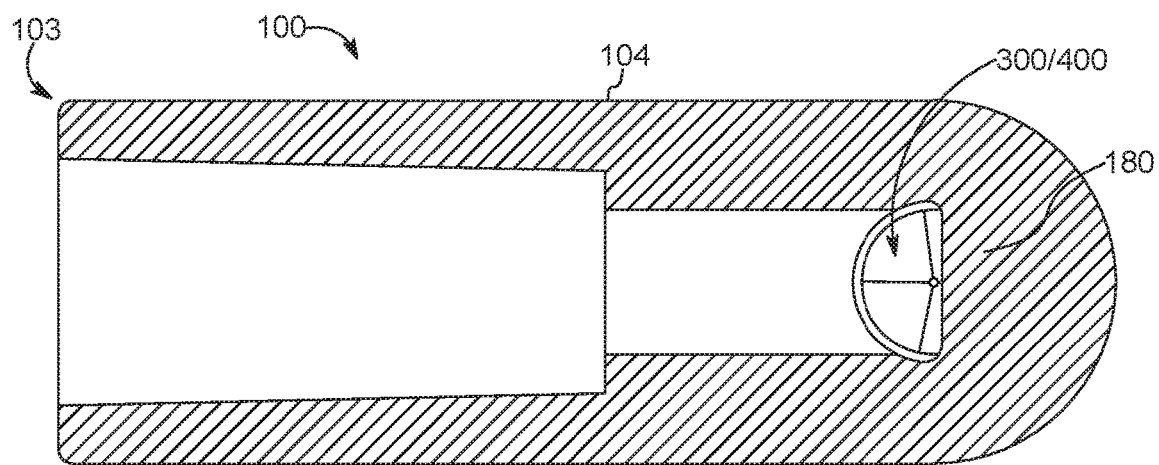
FIG. 21 is a side sectional view of the fluid control valve of FIG. 19.
Figure 22:
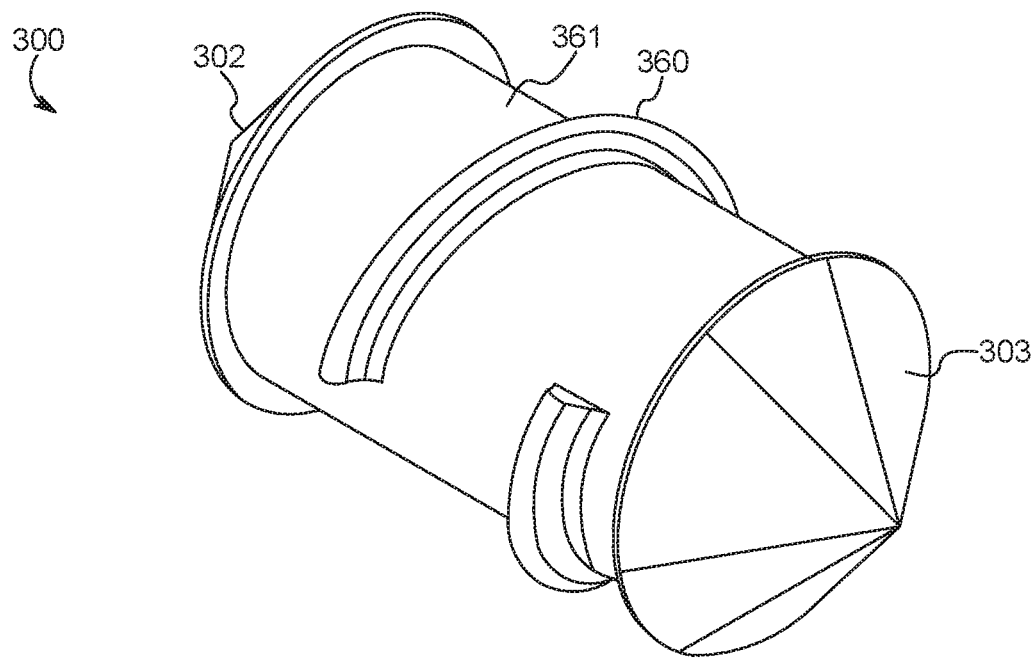
FIG. 22 is a perspective view of a first part of the sliding valve member of the fluid control valve of FIGS. 19-21.
Figure 23:
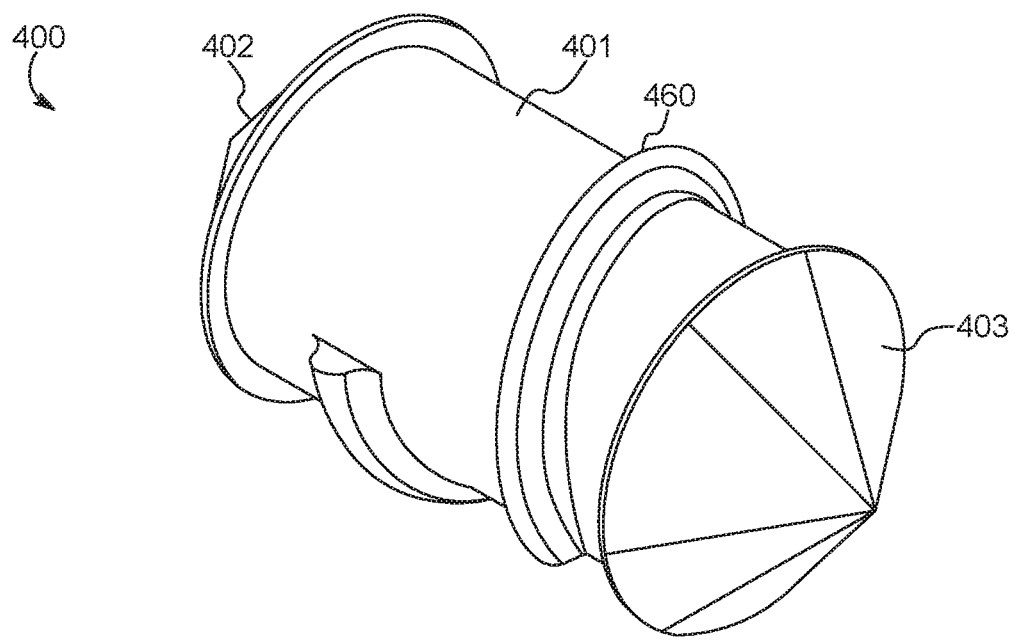
FIG. 23 is a perspective view of a second part of the sliding valve member of the fluid control valve of FIGS. 19-21.

FIG. 20C shows a third operating state where the fluid flow and resulting drag coefficient through the second inlet lumen 132 and the fluid flow and resulting drag coefficient through the first inlet lumen 131 are substantially similar. The second end 303 of the first part sliding valve member 300 and the second end 402 of the second part sliding valve member 400 engage the partition 180. Fluid flow from the first inlet lumen 131 is directed around the helical ridge 360 of the first part sliding valve member 300 and is turbulently mixed with fluid flow from the second inlet lumen 132 directed around the helical ridge 460 of the second part sliding valve member 400. The mixed fluid then flows through the outlet lumen 133.

Figure 24:
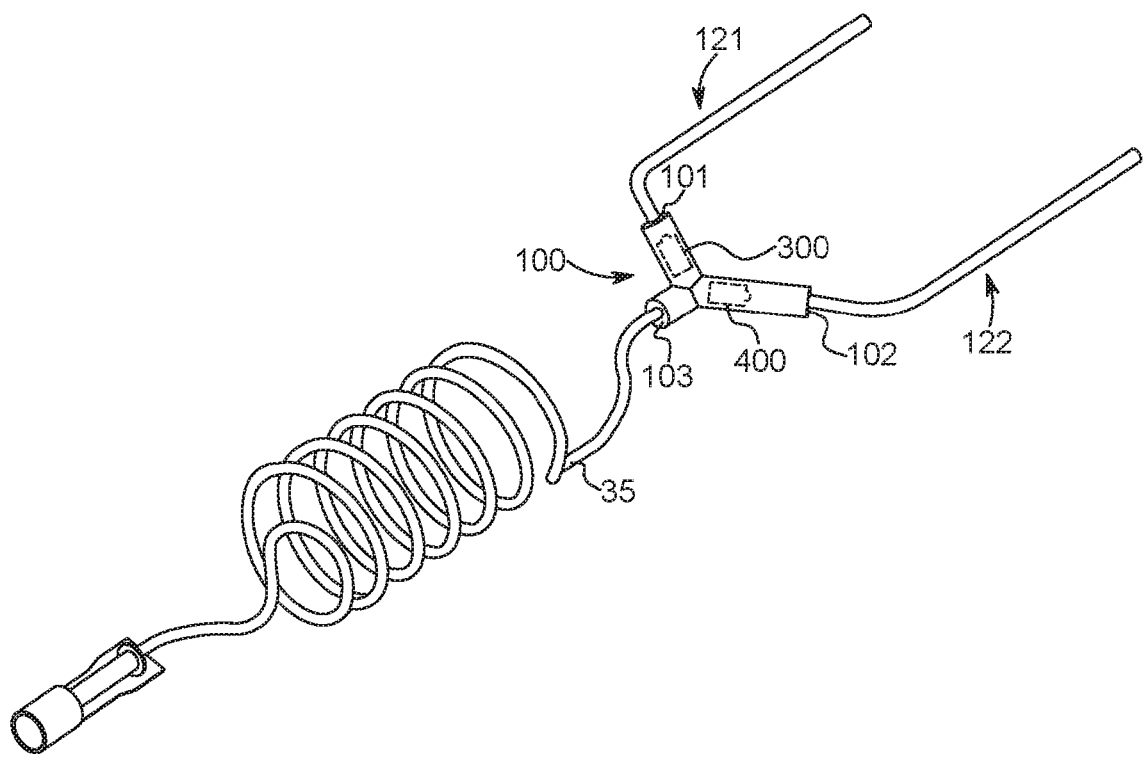
FIG. 24 is a perspective view of another example of a fluid control valve according to the present disclosure.
Figure 25:
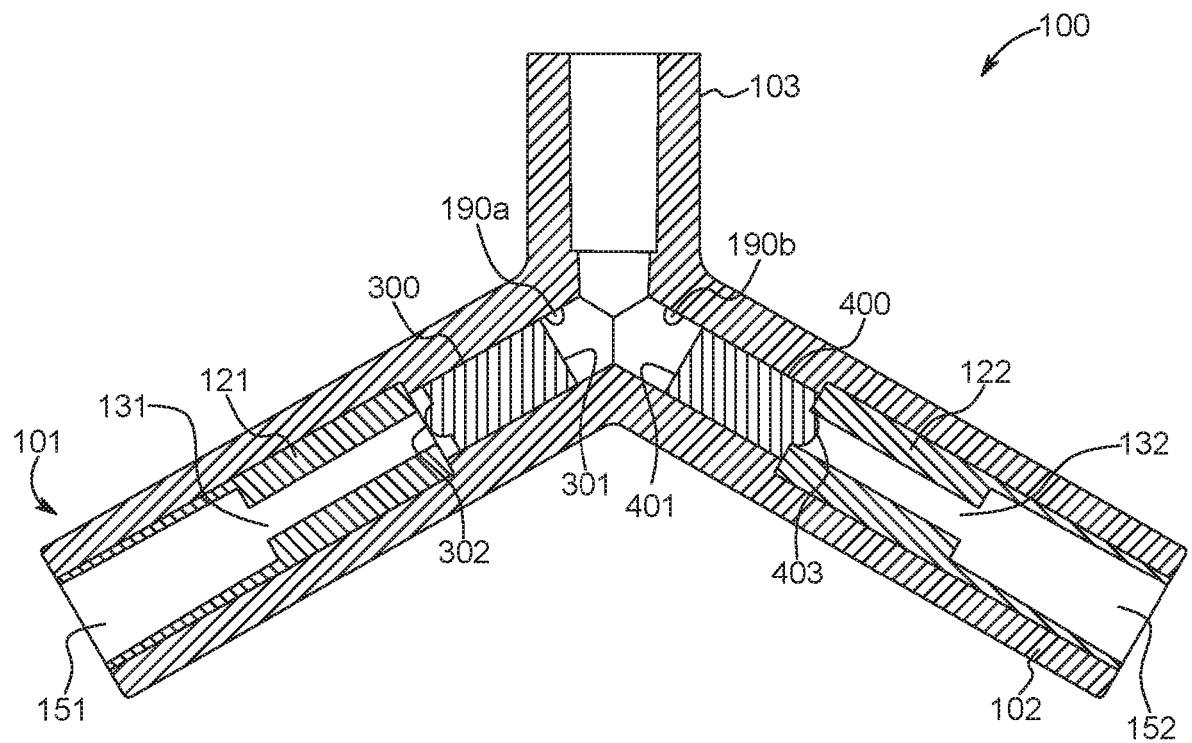
FIG. 25 is a front sectional view of the fluid control valve of FIG. 24.
Figure 26:
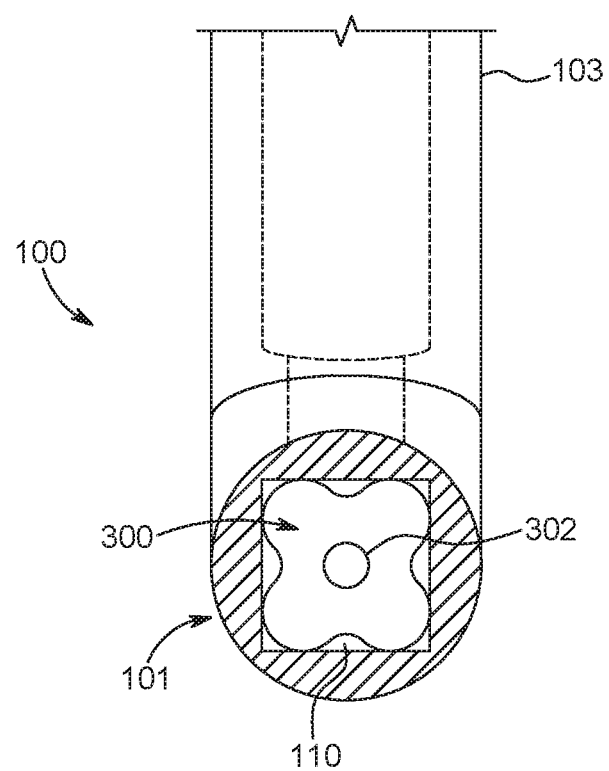
FIG. 26 is a side sectional view of the fluid control valve of FIG. 24.
Figure 27:
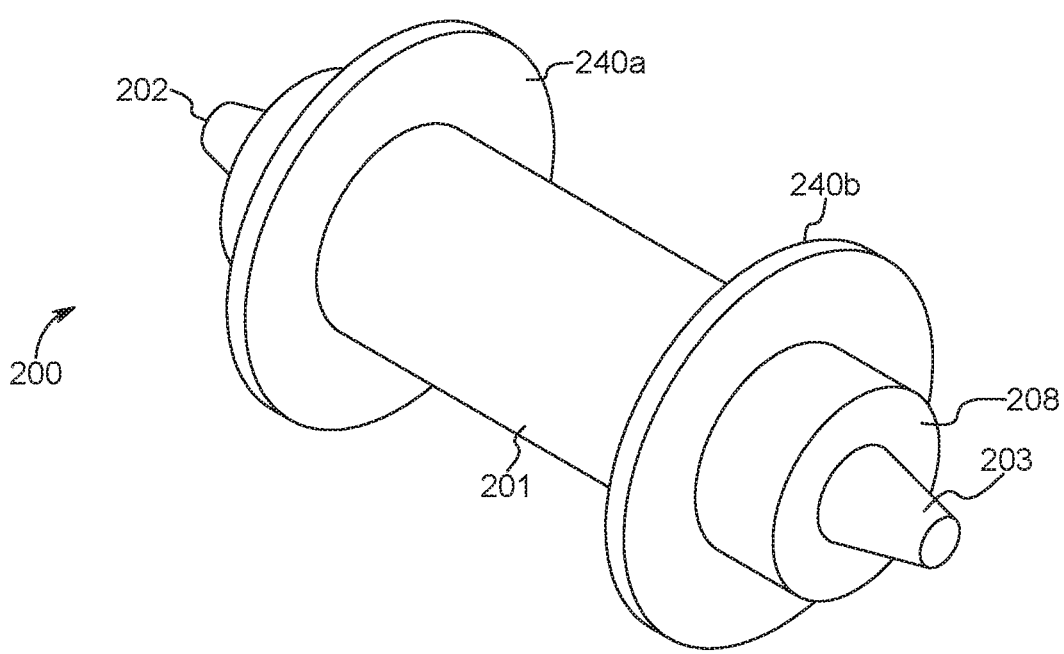
FIG. 27 is a perspective view of a sliding valve member in accordance with another example of the present disclosure.

FIGS. 24-26 depict additional aspects of the fluid control valve 100, the first fluid sliding valve member 300, and the second fluid sliding valve member 400. FIG. 24 shows the fluid control valve 100 in fluid communication with the fluid path set 35. The valve body 104 may be "Y"-shaped and includes a first stop ledge 190a and a second stop ledge 190b protruding into the internal chamber 110 and preventing the first part sliding valve member 300 and the second part sliding valve member 400 from contacting one another. The first stop ledge 190a and the second stop ledge 190b thus provide similar functionality as the partition 180 described with reference to FIGS. 19-23. The first part sliding valve member 300 is freely slidable between the first inlet tube 121 and the first stop ledge 190a. The second part sliding valve member 400 is freely slidable between the second inlet tube 122 and the second stop ledge 190b. In the example shown, the first part sliding valve member 300 and the second part sliding valve member 400 are substantially similar to the example of the sliding valve member 200 shown in FIG. 7, having a hemispherical first sealing end 302 of the first part sliding valve member 300 and a hemispherical second sealing end 403 of the second part sliding valve member 400 although other shapes for the sealing ends are envisioned, as described herein. Operation of the fluid control valve 100 between the first operating state, the second operating state, and the third operating state is substantially as described with reference to examples of the fluid control valve 100 of FIGS. 20A-20C.

FIGS. 27-35 show other examples of the sliding valve member 200 suitable for use in various examples of the fluid control valve 100 having one or more flange members 240. The sliding valve member 200 shown in FIG. 27 has a cylindrical body 201 and annular flange members 240a, 240b, and is suitable for use in a fluid control valve 100 having a circular cross section of the internal chamber 110. The flange members 240a, 240b are shown in the undeflected state. The present disclosure also contemplates other cross-sectional shapes, such as those described herein, and other polygonal cross-sectional shapes. As described herein, the one or more flange members may serve to provide a greater surface area to increase the force applied to the sliding valve member 200 from the fluid pressure, thereby more efficiently moving the sliding valve member 200 to a sealing configuration (i.e., the first or second operating state) when exposed to a fluid pressure differential.

Figure 28:
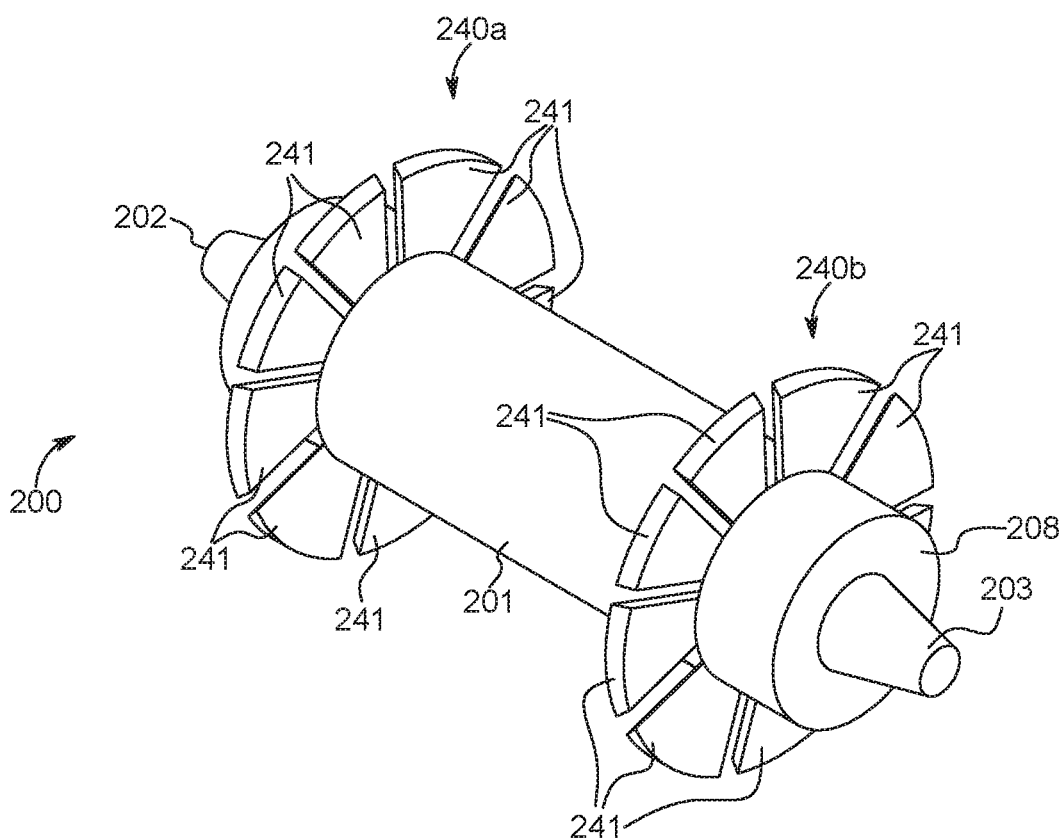
FIG. 28 is a perspective view of a sliding valve member in accordance with another example of the present disclosure.
Figure 29:
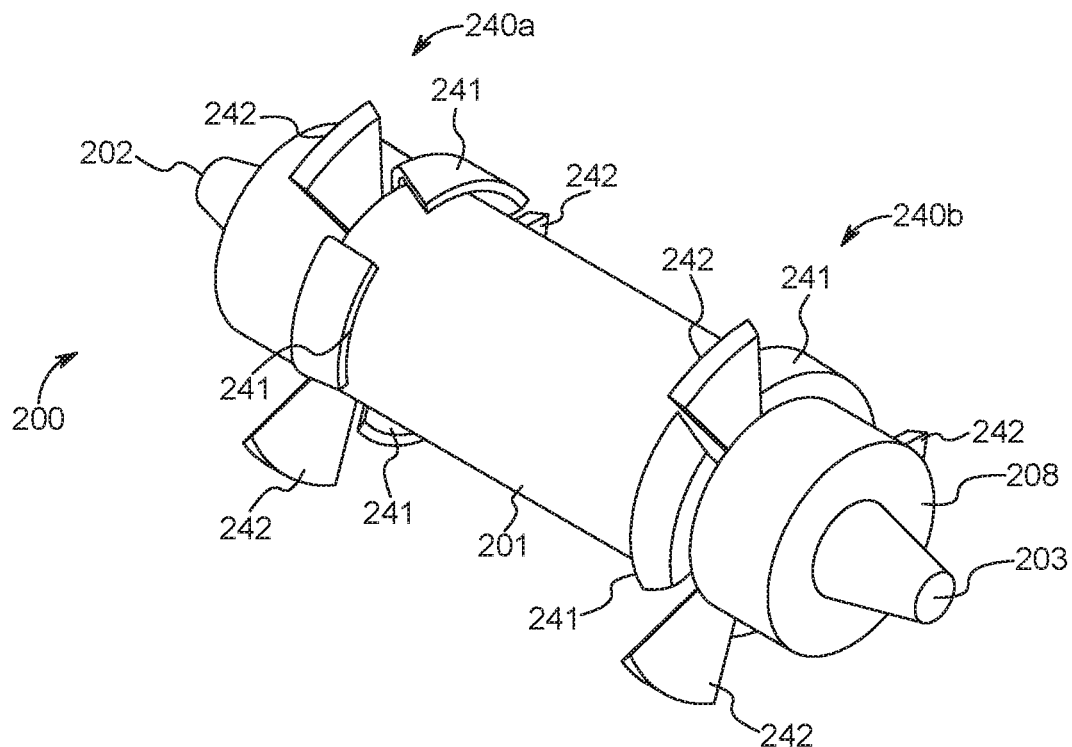
FIG. 29 is a perspective view of a sliding valve member in accordance with another example of the present disclosure.

Various other aspects of the sliding valve members 200 shown in FIGS. 28-29 each have a cylindrical body 201 and cylindrical flange members 240a, 240b having a plurality of flaps 241 separated by slits to allow differential deflection of the flange members and are each suitable for use in a fluid control valve 100 having a circular cross section of the internal chamber 110. Each of the flange members 240a, 240b may be subdivided into a plurality of flaps including one or more resilient flaps 241 optionally with one or more rigid flaps 242. In one aspect shown in FIG. 28, only resilient flaps 241 are illustrated, shown in the undeflected state, which deflect when subjected to fluid pressure above the deflection flow force threshold as described in reference to FIG. 11. In another aspect shown in FIG. 29, alternating resilient flaps 241 and rigid flaps 242 are illustrated. It is to be understood that other arrangements of resilient flaps 241 and rigid flaps 242 may be appreciated by one skilled in the art as being within the scope of the present disclosure. The resilient flaps 241 and rigid flaps 242 may be made from different materials in order to obtain differing stiffness properties. Alternatively, the resilient flaps 241 and rigid flaps 242 may be made of the same material but in different thicknesses such that the resilient flaps 241 are flexible but the rigid flaps 242 are stiff. The resilient flaps 241 are shown in the deflected state. Deflection of the resilient flaps 241 creates a semi-spiral flow of fluid around the sliding valve member 200, inducing mixing of the fluids in the internal chamber 110.

Figure 30:
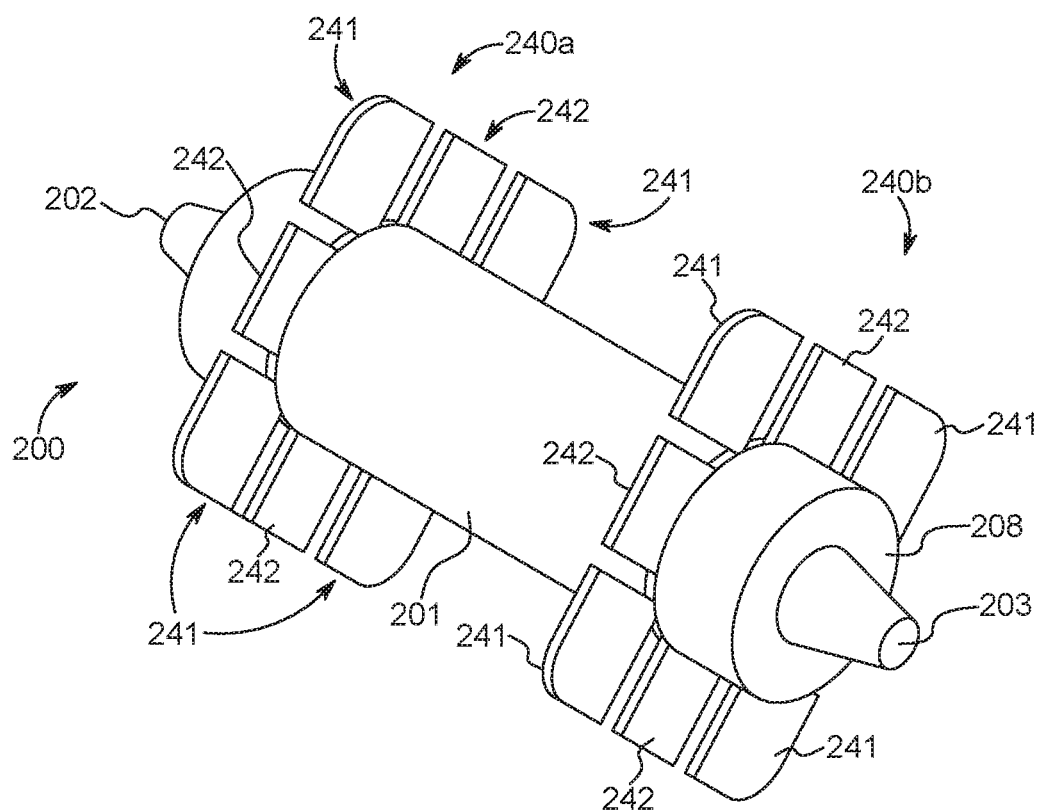
FIG. 30 is a perspective view of a sliding valve member in accordance with another example of the present disclosure.
Figure 31A:
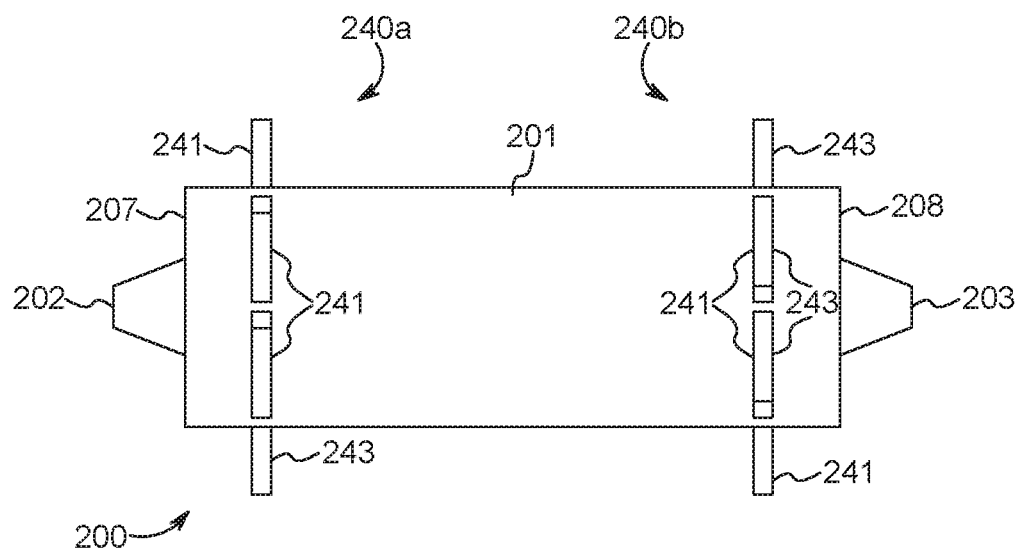
FIGS. 31A-31B are top views of a sliding valve member in accordance with another example of the present disclosure.
Figure 31B:
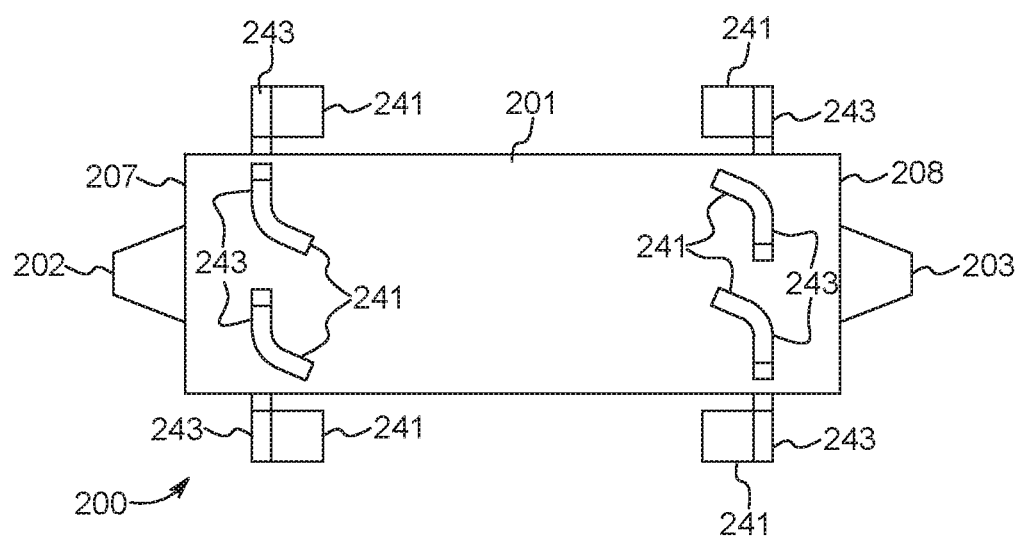

FIG. 30 shows other aspects of the sliding valve member 200 that are similar to the example shown in FIG. 29 except that the flange members 240a, 240b are substantially rectilinear for use in a fluid control valve 100 having a rectilinear cross section of the internal chamber 110. The resilient flaps 241 are shown in the undeflected state Referring now to FIG. 31A-31B, according to other aspects, the resilient flaps 241 may be arranged to deflect about posts 243 extending radially from the longitudinal axis of the sliding valve member 200. Each resilient flap 241 may be integrally formed with the corresponding post 243. In such examples, the posts 243 may be formed of a thicker material than the resilient flaps 241 such that the posts 243 remain rigid while the resilient flaps 241 are deflectable when subjected to sufficient fluid flow force. Alternatively, each resilient flap 241 may be formed separately and adhered to the corresponding post 243. FIG. 31 shows the flaps 241 in the undeflected state, while FIG. 31B shows the flaps in the deflected state.

Figure 32:
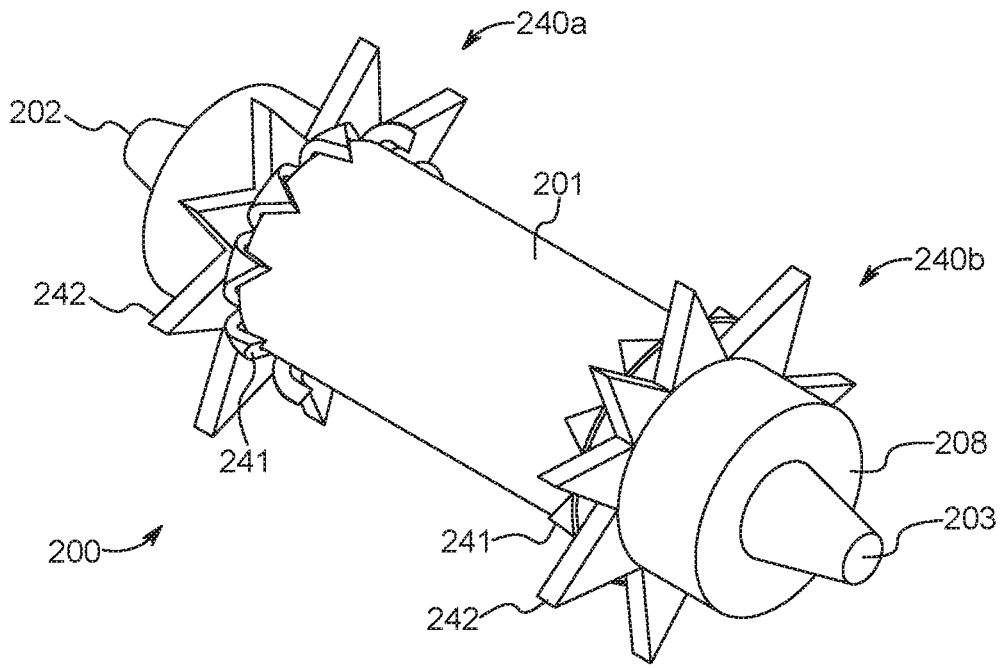
FIG. 32 is a perspective view of a sliding valve member in accordance with another example of the present disclosure.

Referring now to FIG. 32, in certain aspects, each of the flange members 240a, 240b may include a first layer of resilient flaps 241 overlaid with a second layer of rigid flaps 242. The second layer of rigid flaps 242 is arranged on the first layer of resilient flaps 241 such that the rigid flaps 242 are substantially centered in spaces between the resilient flaps 241. The arrangement of the second layer being overlaid and offset from the first layer provides additional surface area for fluid contact. The resilient flaps 241 are shown in the deflected state. In other examples, both the first layer and the second layer are resilient flaps 241.

Figure 33:
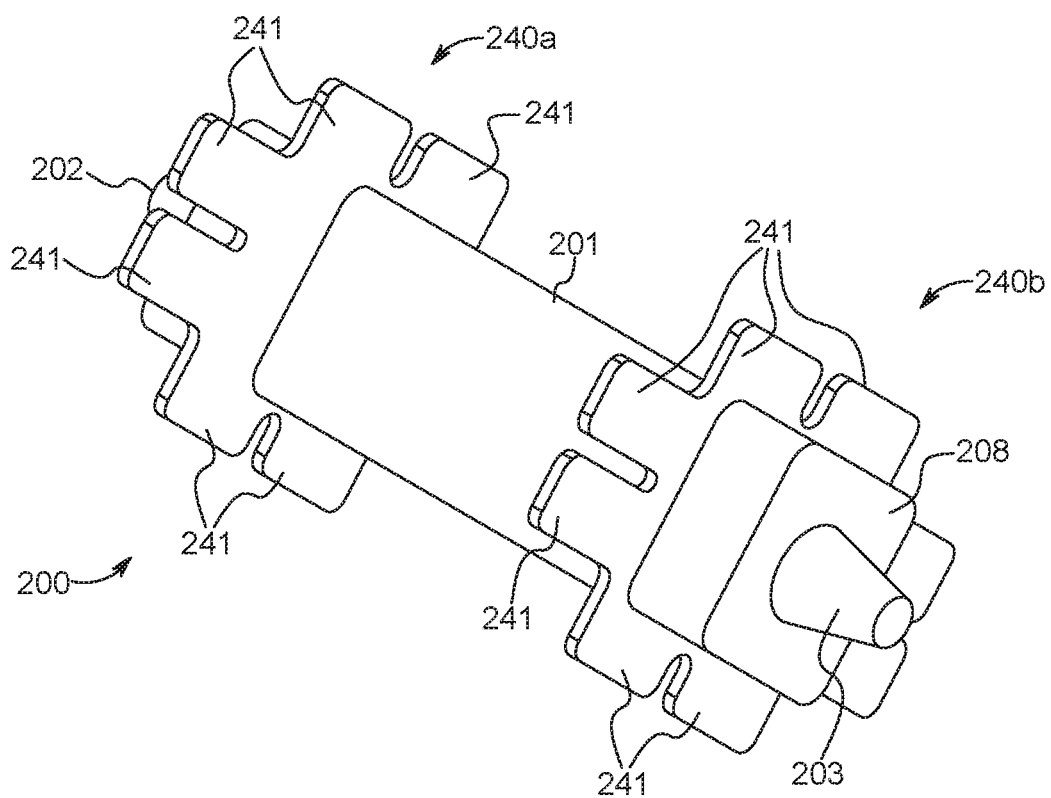
FIG. 33 is a perspective view of a sliding valve member in accordance with another example of the present disclosure.

In various aspects of the sliding valve member 200 shown in FIG. 33 has a rectilinear body 201 and resilient flaps 241 of the flange members 240a, 240b arranged in a cross shape. The sliding valve member 200 is suitable for use in a fluid control valve 100 having a cross-shaped cross section of the internal chamber 110. The resilient flaps 241 are shown in the undeflected state. In other embodiments, one or more of the flaps may be rigid flaps, provided at least one or more of the other flaps are resilient flaps 241.

Figure 34:
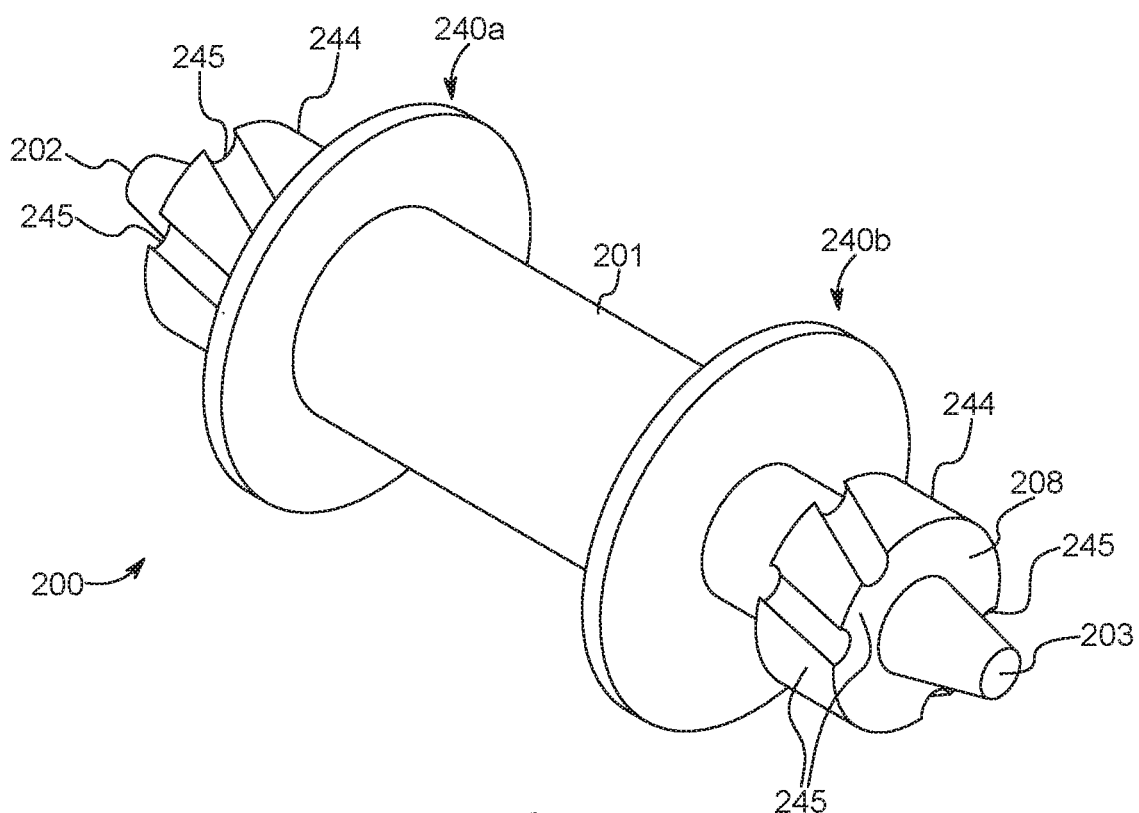
FIG. 34 is a perspective view of a sliding valve member in accordance with another example of the present disclosure.

Other aspects of the sliding valve member 200, as shown in FIG. 34, include enlarged head portions 244 at each end of the body 201. Each head portion 244 may include mixing features, such as fluid veins 245 that impart turbulence to the fluids passing over the head portion 244. The flange members 240a, 240b are shown in the undeflected state.

Figure 35:
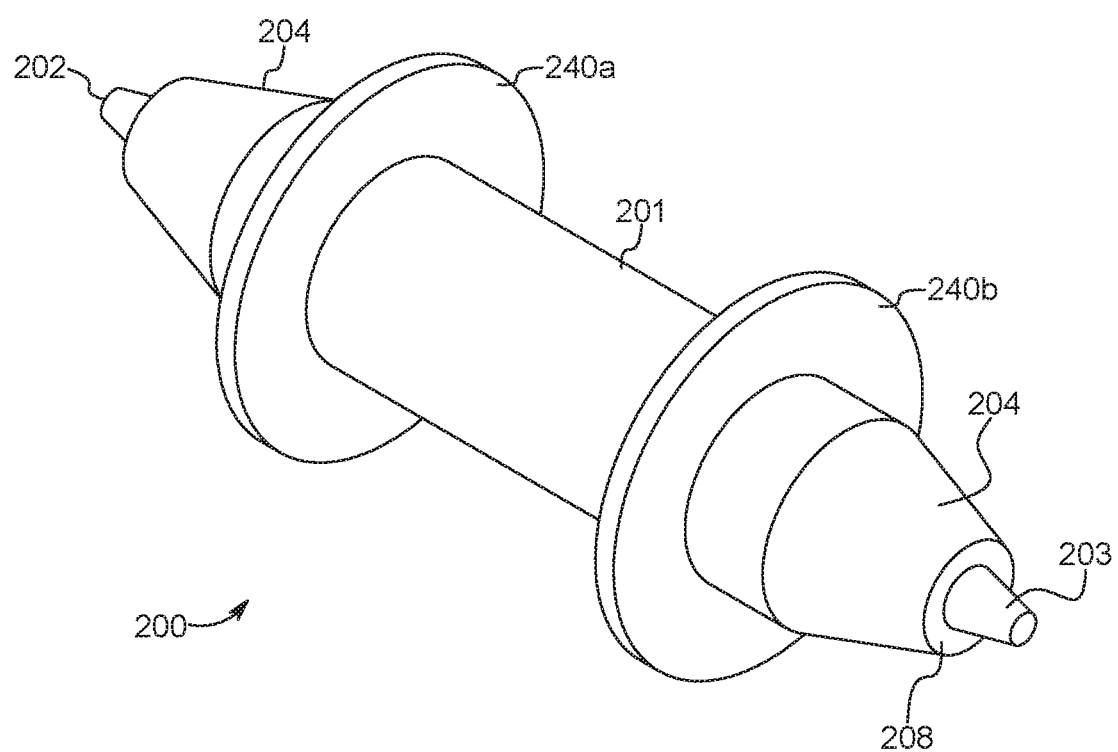
FIG. 35 is a perspective view of a sliding valve member in accordance with another example of the present disclosure.

In various aspects of the sliding valve member 200, as shown in FIG. 35, the first sealing end 202 and second sealing end 203 may include additional tapered portions 204 to facilitate sealing with alternative configurations of the first inlet tube 121 and the second inlet tube 122 of the fluid control valve 100. The flange members 240a, 240b are shown in the undeflected state.

It is to be understood that the various sliding valve members 200 described herein are used for exemplary purposes, and the variations on the features thereof are considered within the spirit of the present disclosure. Further, features of the various sliding valve members 200 may be combined, where practicable, with features of one of more of the several examples described herein.

Figure 36:
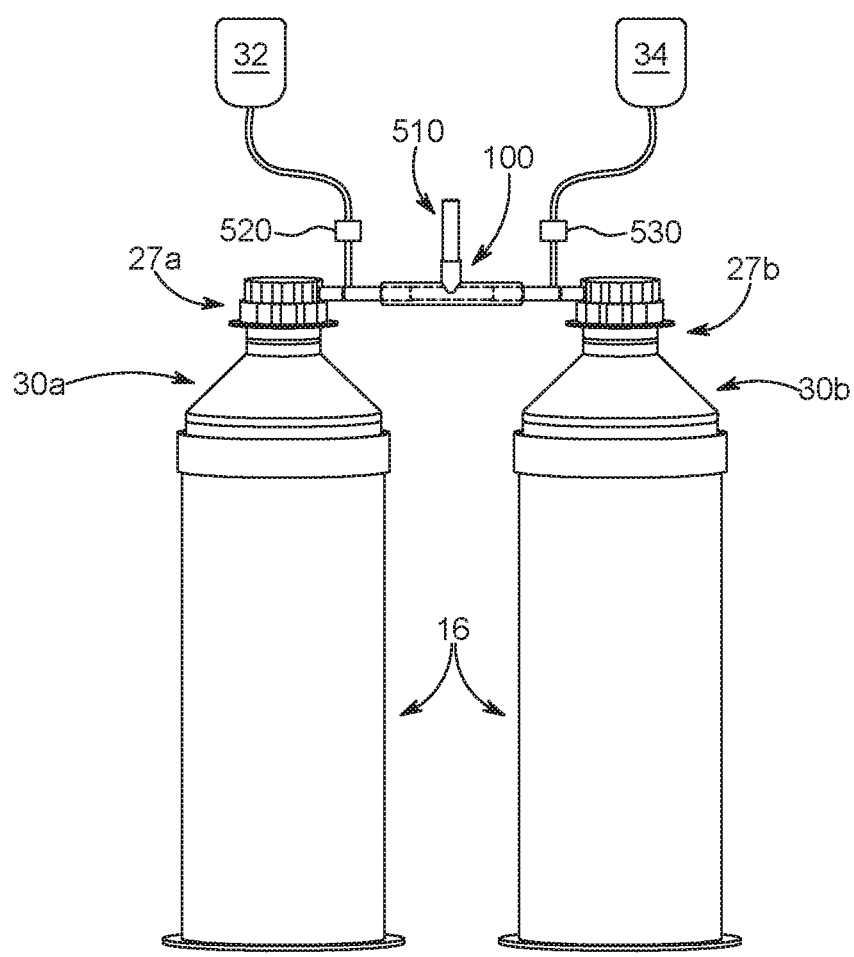
FIG. 36 is a front view of a syringe connector manifold assembly according to the present disclosure.

Other aspects of the present disclosure relate to a syringe connector manifold assembly 500 as shown in FIG. 36. The syringe connector manifold assembly 500 includes the fluid control valve 100 according to any embodiments or combination of aspects described herein, the end cap 27a of the first syringe 30a, and the end cap 27b of the second syringe 30b. The first inlet tube 121 connects the first inlet port 101 of the fluid control valve 100 to the cap 27a of the first syringe 30a, and the second inlet tube 122 connects the second inlet port 102 of the fluid control valve 100 to the end cap 27b of the second syringe 30b. The syringe connector manifold assembly 500 may further include a delivery tube set 510 connecting the outlet port 103 of the fluid control valve 100 to the patient (see, for example, fluid path set 35 in FIG. 2).

In certain embodiments, the syringe connector manifold assembly 500 may further include a first selectable valve 520 connecting the first inlet tube 121 to the first bulk fluid source 32 containing, for example, contrast imaging solution. The syringe connector manifold assembly 500 may further include a second selectable valve 530 connecting the second inlet tube 122 to the second bulk fluid source 34 containing, for example, saline. The first selectable valve 520 and the second selectable valve 530 may be, in some examples, stopcocks or one-way check valves. The first syringe 30a may be filled with fluid from the first bulk fluid source 32 by opening the first selectable valve 520 and retracting the drive member 19 of the fluid injector 10 associated with the plunger or end wall of the first syringe 30a to create a vacuum in the first inlet tube 121. The vacuum draws fluid from the first bulk fluid source 32 into the first inlet tube 121 and ultimately into the first syringe 30a. The applied vacuum also draws the sliding valve member 200 toward the first inlet tube 121, isolating the first inlet tube 121 from the second inlet tube 122 and the delivery tube set 510 so that fluid from the second inlet tube 122 and the delivery tube set 510 are not drawn into the first syringe 30a.

Similarly, the second syringe 30b may be filled with fluid from the second bulk fluid source 34 by opening the second selectable valve 530 and retracting the drive member 19 of the fluid injector 10 associated with the plunger or end wall of the second syringe 30b to create a vacuum in the second inlet tube 122. The vacuum draws fluid from the second bulk fluid source 34 into the second inlet tube 122 and ultimately into the second syringe 30b. The applied vacuum also draws the sliding valve member 200 toward the second inlet tube 122, isolating the second inlet tube 122 from the first inlet tube 121 and the delivery tube set 510 so that fluid from the first inlet tube 121 and the delivery tube set 510 are not drawn into the second syringe 30b. Once filled, the syringe connector manifold assembly 500 may be primed to remove any air bubbles and then used to deliver the first and second fluids to a patient for a medical imaging procedure.

Although the disclosure has been described in detail for the purpose of illustration based on what is currently considered to be the most practical and preferred examples, it is to be understood that such detail is solely for that purpose and that the disclosure is not limited to the disclosed examples, but, on the contrary, is intended to cover modifications and equivalent arrangements. For example, it is to be understood that the present disclosure contemplates that, to the extent possible, one or more features of any example can be combined with one or more features of any other example.

We claim:

1. A fluid control valve for use in a fluid delivery system for delivering fluid to a patient, the fluid control valve comprising:
    a valve body defining an internal chamber;
    a first inlet port for receiving a first inlet tube, wherein the first inlet tube defines a first inlet lumen in fluid communication with the internal chamber, and wherein the first inlet port is in axial alignment with the internal chamber;
    a second inlet port for receiving a second inlet tube, wherein the second inlet tube defines a second inlet lumen in fluid communication with the internal chamber, and wherein the second inlet port is in axial alignment with the internal chamber;
    an outlet port; and
    a sliding valve member disposed in the internal chamber and configured to slide along an axis in the internal chamber between the first inlet port and the second inlet port, the sliding valve member comprising a first sealing end and a second sealing end;
    wherein the sliding valve member is positionable in a first operating state, a second operating state, and a third operating state based on a fluid flow differential between a first fluid in the first inlet lumen and a second fluid in the second inlet lumen; and
    wherein the sliding valve member and the valve body define at least one channel extending between the first sealing end and the second sealing end, wherein the at least one channel provides fluid communication between the second inlet lumen and the outlet port in the first operating state, the at least one channel provides fluid communication between the first inlet lumen and the outlet port in the second operating state, and the at least one channel provides fluid communication between the first inlet lumen, the second inlet lumen, and the outlet port in the third operating state;
    wherein the sliding valve member comprises at least one mixing feature associated with a body of the sliding valve member and configured to provide mixing at a confluence point of the first fluid from the first inlet lumen and the second fluid from the second inlet lumen.

2. The fluid control valve of claim 1, wherein, in the first operating state, the first sealing end of the sliding valve member engages the first inlet tube and isolates the first inlet lumen from the second inlet lumen and the outlet port;
    wherein, in the second operating state, the second sealing end of the sliding valve member engages the second inlet tube and isolates the second inlet lumen from the first inlet lumen and the outlet port; and
    wherein, in the third operating state, the sliding valve member allows fluid communication between the first inlet lumen, the second inlet lumen, and the outlet port.

3. The fluid control valve of claim 2, wherein the sliding valve member comprises at least one flange member extending radially from a body of the sliding valve member.

4. The fluid control valve of claim 3, wherein the at least one flange member comprises at least two flange members, the at least two flange members comprising a first flange member adjacent to the first sealing end and a second flange member adjacent to the second sealing end.

5. The fluid control valve of claim 3, wherein at least a portion of the at least one flange member is deflectable when sufficient fluid flow is applied to a surface of the at least one flange member, wherein deflection of the at least a portion of the at least one flange member allows fluid communication between at least one of the first inlet lumen and the outlet port or between the second inlet lumen and the outlet port.

6. The fluid control valve of claim 3, wherein the at least one flange member comprises one or more deflectable flange members, wherein the one or more deflectable flange members deflect toward a lower flow side in response to the fluid flow differential between the first fluid in the first inlet lumen and the second fluid in the second inlet lumen.

7. The fluid control valve of claim 6, wherein deflection of any of the one or more deflectable flange members increases a drag coefficient of the sliding valve member.

8. The fluid control valve of claim 6, wherein the at least one flange member further comprises one or more rigid flange members.

9. The fluid control valve of claim 3, wherein at least a portion of the at least one flange member is rigid.

10. The fluid control valve of claim 1, wherein the at least one mixing feature comprises one or more helical grooves, one or more helical ridges, one or more channels and one or more projections extending from an outer surface of the sliding valve member.

11. The fluid control valve of claim 10, wherein the one or more helical grooves, one or more helical ridges, one or more channels and one or more projections have opposite directionality.

12. A fluid control valve for use in a fluid delivery system for delivering fluid to a patient, the fluid control valve comprising:
a valve body defining an internal chamber;
a first inlet port for receiving a first inlet tube, wherein the first inlet tube defines a first inlet lumen in fluid communication with the internal chamber;
a second inlet port for receiving a second inlet tube, wherein the second inlet tube defines a second inlet lumen in fluid communication with the internal chamber;
an outlet port; and
a sliding valve member disposed in the internal chamber and configured to slide along an axis in the internal chamber between the first inlet port and the second inlet port, the sliding valve member comprising a first sealing end and a second sealing end;
wherein the sliding valve member is positionable in a first operating state, a second operating state, and a third operating state based on a fluid flow differential between a first fluid in the first inlet lumen and a second fluid in the second inlet lumen; and
wherein the sliding valve member and the valve body define at least one channel extending between the first sealing end and the second sealing end, wherein the at least one channel provides fluid communication between the second inlet lumen and the outlet port in the first operating state, the at least one channel provides fluid communication between the first inlet lumen and the outlet port in the second operating state, and the at least one channel provides fluid communication between the first inlet lumen, the second inlet lumen, and the outlet port in the third operating state,
wherein the sliding valve member comprises a first sliding valve member and a second sliding valve member independently slidable in the internal chamber of the valve body.

13. A syringe connector manifold assembly comprising:
a fluid control valve;
a first syringe end cap;
a second syringe end cap;
a first inlet tube providing fluid communication between a first inlet port of the fluid control valve and the first syringe end cap; and
a second inlet tube providing fluid communication between a second inlet port of the fluid control valve and the second syringe end cap;
wherein the fluid control valve comprises:
a valve body defining an internal chamber axially aligned with the first inlet port and the second inlet port; and
a sliding valve member disposed in the internal chamber and configured to slide along an axis in the internal chamber between the first inlet port and the second inlet port, wherein the sliding valve member is positionable in a first operating state, a second operating state, and a third operating state based on a fluid flow differential between a first fluid in the first inlet tube and a second fluid in the second inlet tube; and
wherein the sliding valve member defines at least one channel extending between the first sealing end and the second sealing end, wherein the at least one channel provides fluid communication between the second inlet port and an outlet port in the first operating state, the at least one channel provides fluid communication between the first inlet port and the outlet port in the second operating state, and the at least one channel provides fluid communication between the first inlet port, the second inlet port, and the outlet port in the third operating state.

14. The syringe connector manifold assembly of claim 13, further comprising:
a first selectable valve providing fluid communication between the first inlet tube and a first bulk fluid source; and
a second selectable valve providing fluid communication between the second inlet tube and a second bulk fluid source.

15. The syringe connector manifold assembly of claim 13, wherein the sliding valve member comprises at least one mixing feature associated with a body of the sliding valve member and configured to provide turbulent mixing at a confluence point of the first fluid injected through the first inlet tube and the second fluid injected through the second inlet tube.

16. The syringe connector manifold assembly of claim 13, further comprising a delivery tube set configured to provide fluid communication between the outlet port of the fluid control valve and a patient.

* * * * *

UNITED STATES PATENT AND TRADEMARK OFFICE
CERTIFICATE OF CORRECTION

PATENT NO. : 11,865,294 B2
APPLICATION NO. : 16/342161
DATED : January 9, 2024
INVENTOR(S) : Spohn et al.

It is certified that error appears in the above-identified patent and that said Letters Patent is hereby corrected as shown below:

In the Specification

In Column 17, Line 13, delete "such a" and insert -- such as a --, therefor.
In Column 19, Line 67, delete "state" and insert -- state. --, therefor.
In Column 20, Line 1, delete "FIG. 31A-31B," and insert -- FIGS. 31A-31B, --, therefor.
In Column 20, Line 54, delete "one of" and insert -- one or --, therefor.

In the Claims

In Column 22, Line 14, in Claim 1, delete "lumen; and" and insert -- lumen; --, therefor.
In Column 22, Line 25, in Claim 1, delete "state;" and insert -- state; and --, therefor.

Signed and Sealed this
Sixteenth Day of April, 2024

Katherine Kelly Vidal
*Director of the United States Patent and Trademark Office*